(12) United States Patent
Hereford et al.

(10) Patent No.: US 12,745,337 B2
(45) Date of Patent: Sep. 22, 2026

(54) LIGHT POLLUTION REDUCTION TECHNIQUES FOR MEDICAL ENVIRONMENTS

(71) Applicant: Stryker Corporation, Kalamazoo, MI (US)

(72) Inventors: Eric Alexander Hereford, North Richland Hills, TX (US); Sean Victor Hastings, Flower Mound, TX (US)

(73) Assignee: Stryker Corporation, Portage, MI (US)

( * ) Notice: Subject to any disclaimer, the term of this patent is extended or adjusted under 35 U.S.C. 154(b) by 76 days.

(21) Appl. No.: 18/542,540

(22) Filed: Dec. 15, 2023

(65) Prior Publication Data

US 2024/0215135 A1 Jun. 27, 2024

Related U.S. Application Data

(60) Provisional application No. 63/476,937, filed on Dec. 22, 2022.

(51) Int. Cl.

| | |
|---|---|
| ***H05B 47/19*** | (2020.01) |
| ***G16H 40/40*** | (2018.01) |
| ***H05B 47/11*** | (2020.01) |
| ***H05B 47/12*** | (2020.01) |
| ***H05B 47/125*** | (2020.01) |
| ***H05B 47/155*** | (2020.01) |
| ***H05B 47/165*** | (2020.01) |

(52) U.S. Cl.

CPC ............. *H05B 47/19* (2020.01); *G16H 40/40* (2018.01); *H05B 47/11* (2020.01); *H05B 47/12* (2020.01); *H05B 47/125* (2020.01); *H05B 47/155* (2020.01); *H05B 47/165* (2020.01)

(58) Field of Classification Search

None

See application file for complete search history.

(56) References Cited

U.S. PATENT DOCUMENTS

| | | | |
|---|---|---|---|
| 5,701,058 | A | 12/1997 | Roth |
| 7,321,385 | B2 | 1/2008 | Rus et al. |
| 9,412,320 | B2 | 8/2016 | Chen et al. |

(Continued)

FOREIGN PATENT DOCUMENTS

| | | | |
|---|---|---|---|
| EP | 3842689 | A1 | 6/2021 |

OTHER PUBLICATIONS

Extended European Search Report dated Feb. 27, 2024, directed to EP Application No. 23219452.2; 13 pages.

(Continued)

*Primary Examiner* — Kenneth B Wells

(74) *Attorney, Agent, or Firm* — Morrison & Foerster LLP

(57) ABSTRACT

Described herein are systems, methods, and programming to control light sources within a medical environment to avoid distracting a user (e.g., surgeon, nurse, medical staff, etc.) and/or inducing alarm fatigue. Some examples include determining that a setting of at least one light source of a medical environment is to be adjusted for use during a medical procedure. A determination may be made that the at least one light source is to be adjusted to a predefined setting associated with the medical procedure. The setting of the at least one light source may be adjusted to the predefined setting. This predefined setting may reduce the likelihood that the emitted light will distract the user while the medical procedure is being performed.

19 Claims, 12 Drawing Sheets

(56) References Cited

U.S. PATENT DOCUMENTS

| | | | | |
|---|---|---|---|---|
| 9,532,424 | B2 | 12/2016 | Arulandu et al. | |
| 9,955,426 | B2 | 4/2018 | Herz et al. | |
| 10,767,822 | B2 * | 9/2020 | Munari | H05B 45/10 |
| 11,240,886 | B2 | 2/2022 | Twaddell et al. | |
| 11,298,118 | B1 * | 4/2022 | Koo | A61B 90/06 |
| 11,659,642 | B1 * | 5/2023 | Hollopeter | H05B 47/155<br>315/153 |
| 12,257,031 | B2 * | 3/2025 | Proske | A61B 90/30 |
| 2005/0099824 | A1 * | 5/2005 | Dowling | A61B 90/36<br>362/572 |
| 2008/0158113 | A1 | 7/2008 | Ozawa | |
| 2008/0219015 | A1 | 9/2008 | Kolstee et al. | |
| 2008/0267467 | A1 * | 10/2008 | Sokulin | A61B 8/461<br>382/128 |
| 2009/0206713 | A1 * | 8/2009 | Vilkas | A61B 50/10<br>362/257 |
| 2013/0310652 | A1 * | 11/2013 | Barsoum | H05B 47/105<br>600/249 |
| 2015/0300816 | A1 * | 10/2015 | Yang | A61B 90/35<br>356/601 |
| 2016/0338795 | A1 * | 11/2016 | Vayser | G02B 27/48 |
| 2019/0180865 | A1 * | 6/2019 | Kashima | A61B 1/00186 |
| 2019/0324253 | A1 * | 10/2019 | Zapata | G02B 21/084 |
| 2020/0008282 | A1 * | 1/2020 | Pereyra | A61B 90/30 |
| 2020/0390392 | A1 * | 12/2020 | Hallack | A61B 90/361 |
| 2021/0220076 | A1 | 7/2021 | Takemoto et al. | |
| 2021/0290046 | A1 * | 9/2021 | Nazareth | A61B 1/00045 |
| 2022/0384011 | A1 | 12/2022 | Shelton, IV et al. | |
| 2023/0329827 | A1 * | 10/2023 | Szuchmacher | F21V 21/15 |
| 2024/0341901 | A1 * | 10/2024 | Hunsdon | A61B 90/35 |

OTHER PUBLICATIONS

Ishihara. (Sep. 2005). "How Far Has the Molecular Alignment of Liquid Crystals Been Elucidated?," Journal of Display Technology 1(1): 30-40.

* cited by examiner

| Light Source ID | Light Setting 0 | Light Setting 1 | . . . | Light Setting M |
| --- | --- | --- | --- | --- |
| Source_ID_0 | Setting_00 | Setting_10 | . . . | Setting_M0 |
| Source_ID_1 | Setting_01 | Setting_11 | . . . | Setting_M1 |
| Source_ID_2 | Setting_02 | Setting_12 | . . . | Setting_M2 |
| . . . | . . . | . . . | . . . | . . . |
| Source_ID_N | Setting_0N | Setting_1N | . . . | Setting_MN |

LIGHT POLLUTION REDUCTION TECHNIQUES FOR MEDICAL ENVIRONMENTS

CROSS-REFERENCE TO RELATED APPLICATIONS

This application claims the benefit of U.S. Provisional Application No. 63/476,937, filed Dec. 22, 2022, the entire contents of which are hereby incorporated by reference herein.

FIELD

The present application generally relates to reducing light pollution within a medical environment.

BACKGROUND

Electronic devices found in operating rooms can include lights that can distract or otherwise bother a surgeon during a surgical procedure. While some lights may be dimmed or turned off, medical staff often can forget to do so. These lights can reduce a clarity of surgical video used by a surgeon while performing certain surgical procedures (e.g., endoscopic procedures). Additionally, these lights can generate alarm fatigue, which is a known problem in operating rooms.

Therefore, it would be beneficial to have systems, methods, and programming controlling lights within a medical environment to avoid distracting a surgeon and/or inducing alarm fatigue.

SUMMARY

Described are systems, methods, and programming for reducing light pollution within a medical environment. Light pollution refers to unwanted light that has the potential to distract a user (e.g., a surgeon, medical staff, etc.) become intrusive to a user while viewing medical images and video, and/or cause alarm fatigue. Alarm fatigue refers to a scenario where medical staff continually check whether one or more alarm lights within the medical environment are trying to notify them of an emergency, when no emergency is occurring. A medical environment (e.g., an operating room) can include many light sources that can contribute to light pollution. These light sources may include, for example, display screens, overhead lights, lights on medical devices, and/or emergency lights. Some of these light sources may lack circuitry to control intensity level and/or blink rate. For example, a blink rate of an LED on a device (e.g., an encoder/decoder device) may not be adjustable. In this scenario, turning the encoder/decoder device off may be the only option to stop the LED from blinking, which may impact patient care.

Some aspects of reducing light pollution can include adjusting a setting of one or more light sources used during a medical procedure. This adjustment may cause an intensity, color, blink rate, and/or other characteristic of the emitted light to change. For example, a setting of a light source may be adjusted to a predefined setting. The predefined setting may indicate a predefined luminosity (e.g., intensity) of light to be emitted by the light source, a predefined blink rate for the light source, a predefined color of the light to be emitted by the light source, etc. This predefined setting may reduce the likelihood that the emitted light will distract a user (e.g., a surgeon, medical staff, etc.) while the medical procedure is being performed. Reducing distractions of medical staff can increase focus on patient care, thereby improving the quality of the medical procedure.

Different contextual prompts, or triggers, may indicate when a light source's setting should be adjusted to the predefined setting. A user may select an option to adjust the setting of the light source to the predefined setting. As another example, conditions associated with the medical procedure being performed may be detected, which can trigger the adjustment of the light source's setting. The conditions may include an ambient light level of the medical environment being less than or equal to a threshold ambient light level associated with the medical procedure being performed within the medical environment. The conditions may instead or additionally include one or more objects or actions associated with the medical procedure being detected. For example, images depicting the medical environment, intra-operative images, or other images may be analyzed to determine whether any medical objects are present. If one or more particular medical objects are detected in the images, it may be determined that the medical procedure has entered a particular phase associated with the detected medical object(s), and therefore the setting of the light source should be adjusted based on the phase.

Adjusting the color, brightness, blink rate, etc. of one light source may cause another light source's setting to be adjusted. For example, a surgical light and/or an overhead light may adjust from emitting white light to emitting green light, and based on this adjustment, instructions may be provided to adjust other light sources within the medical environment. As another example, adjusting a brightness, contrast, clarity, or other setting of a display device may cause instructions to be provided to one or more light sources within the medical environment to adjust the one or more light sources based on the adjustment of the display device. Alternatively or additionally, adjustments to a setting of one or more light sources may cause instructions to be provided to a display device to adjust a setting of the display device. In each of the aforementioned examples, the adjustment of settings of one or more light sources and/or display devices may indicate that a medical procedure and/or phase within the medical procedure has begun and/or ended. For example, turning a first light source off may indicate that a medical procedure has entered a particular phase. Instructions may be provided to adjust a second light source within the medical environment based on the first light source's setting being adjusted.

According to some examples, a method includes: determining that a setting of at least one light source of a medical environment is to be adjusted for use during a medical procedure; determining that the at least one light source is to be adjusted to a predefined setting associated with the medical procedure; and causing the setting of the at least one light source to be adjusted to the predefined setting.

In any of the examples, determining that the setting of the at least one light source is to be adjusted can include: receiving, by a device of the medical environment, a selection to use the medical environment for the medical procedure, the device being communicably coupled to the at least one light source; and sending, by the device, a notification to the at least one light source, the notification indicating that the setting of the at least one light source is to be adjusted.

In any of the examples, determining that the setting of the at least one light source is to be adjusted can include:

identifying that a setting of at least one medical light of the medical environment has been adjusted for use during the medical procedure.

In any of the examples, determining that the setting of the at least one light source is to be adjusted can include: determining, using one or more optical sensors of the medical environment, that an ambient light of the medical environment has been adjusted for use during the medical procedure, the setting being adjusted based at least in part on the ambient light.

In any of the examples, determining that the setting of the at least one light source is to be adjusted can include: receiving, from an image sensor of the medical environment, one or more images depicting the medical environment; and detecting, using a machine learning model, at least one medical object associated with the medical procedure within the one or more images, the setting being adjusted based at least in part on the at least one medical object being detected.

In any of the examples, determining that the setting of the at least one light source is to be adjusted can include: receiving, from an image sensor of the medical environment, one or more images depicting the medical environment; and identifying, using one or more machine learning models, an activity of a user within the medical environment based on the one or more images, the setting being adjusted based at least in part on the activity of the user.

In any of the examples, wherein determining that the setting of the at least one light source is to be adjusted comprises: accessing scheduling data associated with the medical environment, the setting being adjusted based at least in part on the scheduling data.

In any of the examples, determining that the setting of the at least one light source is to be adjusted can include: receiving, using one or more image sensors, one or more images depicting the medical environment; and determining an ambient light level of the medical environment based on the one or more images, the setting being adjusted based at least in part on the ambient light level.

In any of the examples, determining that the setting of the at least one light source is to be adjusted can include: detecting, using one or more audio sensors, a voice command to adjust the setting of the at least one light source.

In any of the examples, the method can further include: sending an instruction to a display screen within the medical environment, the instruction indicating that a brightness of the display screen is to be reduced to a predefined brightness level.

In any of the examples, determining that the setting of the at least one light source is to be adjusted can include: detecting, using one or more optical sensors, light emitted by a medical light within the medical environment, the emitted light being associated with a light profile; and determining the light profile of the light, the setting being adjusted based at least in part on the light profile.

In any of the examples, determining that the setting of the at least one light source is to be adjusted can include: detecting, using one or more optical sensors, light emitted by one or more additional light sources within the medical environment; and determining that a setting of the light emitted by the one or more additional light sources has been adjusted to be the predefined setting.

In any of the examples, the method can further include: receiving an instruction to adjust the at least one light source to a new setting differing from the predefined setting; and updating the predefined setting to be the new setting.

In any of the examples, determining that the setting of the at least one light source is to be adjusted can include: detecting, using a motion sensor of a medical device used for the medical procedure, motion indicative of the medical device being used for the medical procedure.

In any of the examples, determining that the setting of the at least one light source is to be adjusted can include: designating an optical sensor within the medical environment for use in detecting an ambient light level of the medical environment; and determining, using the optical sensor, the ambient light level of the medical environment, the setting being adjusted based at least in part on the ambient light level.

In any of the examples, determining that the setting of the at least one light source is to be adjusted can include: identifying one or more light sources of a plurality of light sources within the medical environment that had a respective setting adjusted to the predefined setting; and determining a location of the one or more light sources with respect to the at least one light source, the setting being adjusted based on a quantity of the one or more light sources and the location of the one or more light sources.

In any of the examples, the method can further include: determining an ambient light level of the medical environment subsequent to the at least one light source being adjusted to the predefined setting; and causing light emitted by one or more medical lights of the medical environment to be adjusted for use during the medical procedure based on the ambient light level.

In any of the examples, the method can further include: detecting an ambient light level of the medical environment subsequent to the at least one light source being adjusted to the predefined setting; determining, based on the ambient light level, that the medical procedure has completed; and causing the setting of the at least one light source to be adjusted to default setting corresponding to completion of the medical procedure.

In any of the examples, the method can further include: disabling the at least one light source from emitting light based on the setting being adjusted.

In any of the examples, the medical environment can include a surgical suite.

In any of the examples, the medical procedure can be a surgical procedure.

In any of the examples, the predefined setting associated with the medical procedure can include a predefined intensity level of light to be output by the at least one light source.

In any of the examples, the predefined intensity level of the light can include a percentage of a maximum luminosity of the at least one light source.

In any of the examples, the predefined setting associated with the medical procedure can include a predefined color of light to be output by the at least one light source.

In any of the examples, the predefined setting associated with the medical procedure can include a predefined blink rate of light to be output by the at least one light source.

According to some examples, a system comprises a controller programmed to effectuate the method of any one of the examples.

According to some examples, a non-transitory computer-readable medium stores computer program instructions that, when executed by one or more processors, effectuate the method of any of the examples.

According to some examples, a computer program product comprises software code portions comprising instructions that, when executed by one or more processors, effectuate the method of any of the examples.

It will be appreciated that any of the variations, aspects, features, and options described in view of the systems apply equally to the methods and vice versa. It will also be clear that any one or more of the above variations, aspects, features, and options can be combined.

BRIEF DESCRIPTION OF THE FIGURES

The invention will now be described, by way of example only, with reference to the accompanying drawings, in which.

DETAILED DESCRIPTION

Figure 1A:
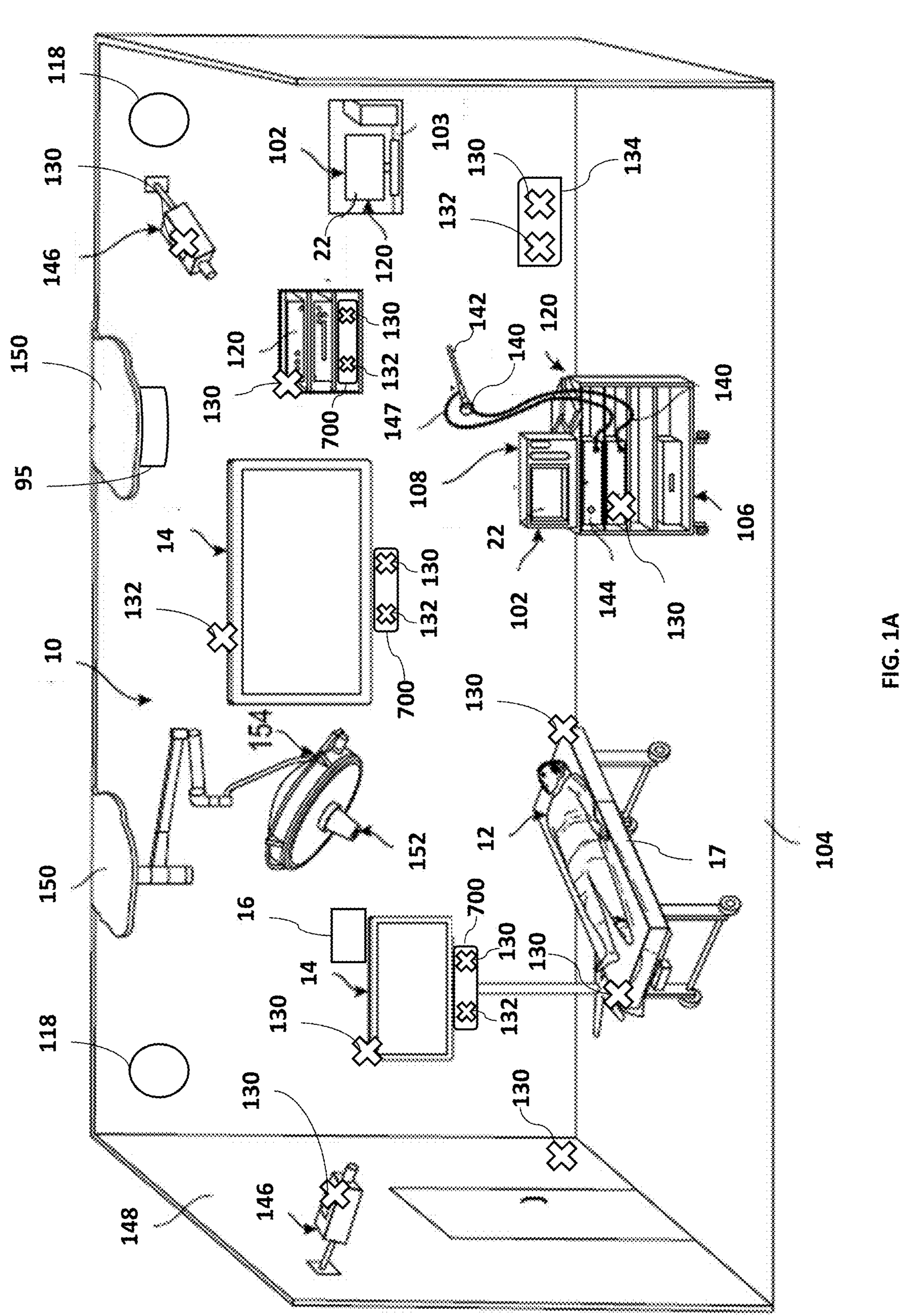
FIG. 1A illustrates an example medical environment, according to some aspects.

Reference will now be made in detail to implementations and various aspects and variations of systems and methods described herein. Although several example variations of the systems and methods are described herein, other variations of the systems and methods may include aspects of the systems and methods described herein combined in any suitable manner having combinations of all or some of the aspects described.

Described are systems, methods, and programming for reducing light pollution within a medical environment. Light pollution refers to unwanted light that has the potential to distract a user (e.g., a surgeon, medical staff, etc.), be intrusive to viewing medical images and video, and/or cause alarm fatigue. A medical environment (e.g., an operating room) can include many light sources that can contribute to light pollution. These light sources may include, for example, display screens, overhead lights, lights on medical devices, and/or emergency lights. Some medical procedures may be performed using minimally invasive techniques. These medical procedures may use small medical devices including cameras (e.g., endoscopes) to allow a user (e.g., a surgeon, a nurse, medical staff, etc.) to view internal portions of a patient without requiring large incisions. The cameras may stream a surgical video feed of the internal portions of the patient to a display device, which may be viewed by the user. The user may use the surgical video feed to perform the medical procedure in lieu of making larger incisions to expose those same internal portions of the patient. Accordingly, because the surgical video feed is such an integral component of the medical procedure, ensuring that it is clearly viewable by users (e.g. a surgeon) is paramount.

The medical environment may be populated by many devices that include light sources. For example, a medical environment may comprise one or more encoder/decoder devices, display devices, surgical lights, overhead lights, etc. These devices may emit light in different colors (e.g., white light, green light, etc.), at different blink rates, at different intensities, and/or having other characteristics. Furthermore, the light emitted by certain light sources may differ and/or adjust as the medical procedure progresses.

Alarm fatigue can also affect users in the medical environment. Alarm fatigue refers to a scenario where users (e.g., surgeons, nurses, medical staff, etc.) continually check whether one or more alarm lights within the medical environment are trying to notify them of an emergency, when no emergency is occurring. In addition to bothering users in the medical environment, these light sources may decrease the clarity, contrast, brightness, viewability, or other aspects of the surgical video feed being displayed. For example, these light sources may introduce glare on display devices presenting the surgical video feed. It would therefore be desirable to adjust a setting of these light sources during medical procedures to ensure that there is no decrease in clarity, contrast, brightness, etc., of the displayed surgical video feed. However, the number of light sources in the medical environment, their respective locations within the medical environment, and/or the adjustments that need to be made to those light sources may contribute to the difficulty in manually and/or programmatically adjusting each light source to the desired setting.

Technical solutions described herein provide systems and methods for determining when to adjust a setting of one or more light sources within a medical environment. The technical solutions described herein may determine a setting with which to adjust the one or more light sources, and based on the determined setting, may cause the one or more light sources to be adjusted to a pre-determined setting. Thus, a technical effect of these technical solutions may be an increase in clarity, contrast, and visibility of images displayed on a display device within the medical environment. Another technical effect of these technical solutions may be a reduction in alarm fatigue for medical staff within the medical environment, thereby increasing focus on the patient and the medical procedure being performed.

Different contextual prompts, or triggers, may indicate that a setting of a light source is to be adjusted. For example, a user may select an option displayed on a touchscreen interface, a physical button or switch, and/or another input mechanism, which may indicate that the light source's setting is to be adjusted. As another example, an ambient light level of the medical environment being less than a threshold ambient light level may indicate that light source's setting is to be adjusted. The setting adjustment may place the light source in a mode associated with a medical procedure being performed. This mode may be referred to as a "dark mode," a "medical procedure mode," and/or a "minimally invasive surgical (MIS) mode." Entering into this mode or being placed in this mode may cause an instruction to be sent to one or more light sources. The instruction may cause a light profile of the one or more light sources to be adjusted to a predefined setting associated with the medical procedure mode. As an example, placing a light source in the medical procedure mode may cause an intensity, a blink rate, a hue, a color, and/or other characteristics of light that may be emitted by the light source to be adjusted to a predefined intensity, blink rate, hue, color, etc. The predefined intensity (e.g., X % of the light source's maximum luminosity and/or turning the light source off entirely), blink rate (e.g., 10 or more blinks per minute (bpm), 60 or more bpm, 100 or more bpm, etc.), hue (e.g., having a hue angle between 0 and 360 degrees), and/or color (e.g., red, yellow, green, blue, violet, etc.) of the emitted light may be selected to minimally impact visibility of surgical video feeds, reduce distractions for the user (e.g., a surgeon, a nurse, medical staff, etc.), and/or prevent alarm fatigue.

Determining when the setting of a light source is to be adjusted may include detecting that another device within the medical environment has been adjusted during the medical procedure. For example, an overhead light and/or a surgical light may be adjusted from a first setting to a second setting. The first setting may have a higher or lower intensity, different color, or other differences, when compared to the second setting. Based on the overhead light and/or surgical light being adjusted from the first setting to the second setting, one or more light sources in the medical environment may also be adjusted to a predefined setting. The predefined setting may correspond to a setting of the light source that minimizes potential distractions to a user (e.g., a surgeon, medical staff, etc.). As an example, the predefined setting may include a predefined luminosity, intensity, power, and/or other characteristic of light emitted by the light source. The predefined luminosity, intensity, power, etc. may be represented as a comparison to a maximum luminosity, intensity, and/or power of the light source. For example, the predefined setting may indicate that the light source is to emit light at 10% of its maximum luminosity.

The light source may be adjusted based on an ambient light level of the medical environment. For example, one or more devices within the medical environment may include an ambient light sensor. If the ambient light sensor detects that the ambient light level is less than or equal to a threshold ambient light level, then one or more light sources in the medical environment may be adjusted to a predefined setting associated with the medical procedure being performed.

As described herein, machine learning models may be used to determine whether a setting of a light source is to be adjusted during a medical procedure. For example, cameras disposed within the medical environment may capture images of the medical environment. Machine learning models may analyze these images to identify activities of individuals within the medical environment (e.g., medical staff). If the machine learning models determine that the identified activities are associated with the medical procedure, then the machine learning models may cause a setting of a light source to be adjusted to a predefined setting associated with the medical procedure. Machine learning models may instead or additionally be employed to analyze the images of the medical environment to determine an ambient light level. If the machine learning models determine that the ambient light level is less than or equal to a threshold ambient light level, then the machine learning models may cause a setting of a light source to be adjusted to the predefined setting associated with the medical procedure. Machine learning models may instead or additionally be employed to analyze the surgical video feed and detect whether the surgical video feed is displaying images depicting objects and/or activities associated with the medical procedure. For example, machine learning models may be trained to identify anatomical structures within the surgical video feed. The presence of certain anatomical structures may indicate that a particular medical procedure is being performed, and that medical procedure is at a particular phase of the medical procedure (e.g., a preoperative phase, an intraoperative phase, a postoperative phase, etc.). The light sources may be instructed to adjust their settings to a predefined setting associated with the medical procedure based on the phase of the medical procedure.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating," or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general-purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. Suitable processors include central processing units (CPUs), graphical processing units (GPUs), field-programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

It should also be noted that although some aspects are described herein with respect to machine learning models, other prediction models (e.g., statistical models or other analytics models) may be used in lieu of or in addition to machine learning models (e.g., a statistical model replacing a machine-learning model and a non-statistical model replacing a non-machine-learning model).

FIG. 1A illustrates an example medical environment 10, according to some aspects. Medical environment 10 may represent a surgical suite, operating room, or other care environment where a medical procedure may be performed. Medical environment 10 may include devices used to perform a medical procedure on a patient 12. Such devices may include one or more sensors, one or more medical devices, one or more display devices, one or more light sources, one or more computing devices, or other components. For example, at least one medical device 120 may be located within medical environment 10. Medical device 120 may be used to assist medical staff performing a medical procedure (e.g., surgery). Medical device 120 may be used to document events and information regarding the medical procedure. For example, medical device 120 may be used to input and/or receive patient information (e.g., to/from electronic medical records (EMRs), from electronic health records (EHRs), from Hospital Information Systems (HIS), communicated in real-time from another system, etc.). The received patient information may be saved onto medical device 120. Alternatively or additionally, the patient information may be displayed using medical device 120. In some aspects, medical device 120 may be used to record patient information. For example, medical device 120 may be used to store the patient information in an EMR, EHR, HIS, or other database.

Medical device 120 may be capable of obtaining, measuring, detecting, and/or saving information related to the patient 12. Medical device 120 may or may not be coupled to a network that includes records of patient 12, for example, an EMR, EHR, or HIS. Medical device 120 may include or be integrated with a computing system 102 (e.g., a desktop computer, a laptop computer, a tablet device, etc.) having an application server. For example, medical device 120 may include processors or other hardware components that enable data to be captured, stored, saved, and/or transmitted to other devices. Computing system 102 can have a motherboard that includes one or more processors or other similar control devices as well as one or more memory devices. The processors may control the overall operation of computing system 102 and can include hardwired circuitry, programmable circuitry that executes software, or a combination thereof. The processors may, for example, execute software stored in the memory device. The processors may include, for example, one or more general- or special-purpose programmable microprocessors and/or microcontrollers, graphics processing unit (GPU), tensor processing unit (TCU), application specific integrated circuits (ASICs), programmable logic devices (PLDs), programmable gate arrays (PGAs), etc. The memory devices may include any combination of one or more random access memories (RAMs), read-only memories (ROMs) (which may be programmable), flash memory, and/or other similar storage devices. Patient information may be inputted into computing system 102 (e.g., making an operative note during the medical or surgical procedure on patient 12 in medical environment 10) and/or computing system 102 can transmit the patient information to another medical device 120 (via either a wired connection or wirelessly).

Computing system 102 can be positioned in medical environment 10 on a table (stationary or portable), a floor 104, a portable cart 106, an equipment boom, and/or a shelving 103. FIG. 1A illustrates two forms of computing system 102: a first computing system 102 in the form of a desktop computer on shelving 103 and a second computing system 102 incorporated into an imaging system 108 on portable cart 106. It is to be understood that medical environment 10 may include any number of computer systems.

In some aspects, medical environment 10 may be an integrated suite used for minimally invasive surgery (MIS) or invasive procedures. Video and audio components and associated routing may be located throughout medical environment 10. For example, monitor 14 may present video and speakers 118 may output audio. The components may be located on or within the walls, ceilings, and/or floors of medical environment 10. For example, room cameras 146 may be mounted to walls 148 or a ceiling 150. Wires, cables, and hoses can be routed through suspensions, equipment booms, and/or interstitial space. The wires, cables, and/or hoses in medical environment 10 may be capable of connecting to mobile equipment, such as portable cart 106, C arms, microscopes, etc. to communicate audio, video, and other data information.

Imaging system 108 may be configured to capture images and/or video, and may route audio, video, and other data (e.g., device control data) throughout medical environment 10. Imaging system 108 and/or associated router(s) may route the information between devices within or proximate to medical environment 10. In some aspects, imaging system 108 and/or associated router(s) (not shown) may be located external to medical environment 10 (e.g., in a room outside of an operating room), such as in a closet. As an example, the closet may be located within a predefined distance of medical environment 10 (e.g., within 325 feet, or 100 meters). In some aspects, imaging system 108 and/or the associated router(s) may be located in a cabinet inside or adjacent to medical environment 10.

The captured images and/or videos may be displayed via one or more display devices. For example, images captured by imaging system 108 may be displayed using monitor 14. Imaging system 108, alone or in combination with one or more audio sensors, may also be capable of recording audio, outputting audio, and/or a combination thereof. In some aspects, patient information can be inputted into imaging system 108 and added to the images and videos recorded and/or displayed. Imaging system 108 can include internal storage (e.g., a hard drive, a solid-state drive, etc.) for storing the captured images and videos. Imaging system 108 can also display any captured and/or saved images (e.g., from the internal hard drive). For example, imaging system 108 may cause monitor 14 to display a saved image. As another example, imaging system 108 may display a saved video using a touchscreen monitor 22. Touchscreen monitor 22 and/or monitor 14 may be coupled to imaging system 108 via a wired connection and/or wirelessly. It is contemplated that imaging system 108 could obtain or create images of patient 12 during a medical or surgical procedure from a variety of sources (e.g., from video cameras, video cassette recorders, X-ray scanners (which convert X-ray films to digital files), digital X-ray acquisition apparatus, fluoroscopes, computed tomography (CT) scanners, magnetic resonance imaging (MRI) scanners, ultrasound scanners, charge-coupled (CCD) devices, and other types of scanners (handheld or otherwise)). If coupled to a network, imaging system 108 can also communicate with a picture archiving and communication system (PACS), as is well known to those skilled in the art, to save images and videos in the PACS and to retrieve images and videos from the PACS. Imaging system 108 can couple to and/or integrate with an electronic medical records database (e.g., EMR), a Hospital Information Systems (HIS), and/or a media asset management database.

Touchscreen monitor 22 and/or monitor 14 may display images and videos captured live by imaging system 108. Imaging system 108 may include at least one image sensor, for example, disposed within camera head 140. Camera head 140 may be configured to capture an image or a sequence of images (e.g., video frames) of patient 12. Camera head 140 can be a hand-held device, such as an open-field camera or an endoscopic camera. For example, imaging system 108 may be coupled to an endoscope 142, which may include or be coupled to camera head 140. Imaging system 108 may communicate with a camera control unit 144 via a fiber optic cable 147.

Room cameras 146 may also be configured to capture an image or a sequence of images (e.g., video frames) of medical environment 10. The captured image(s) may be displayed using touchscreen monitor 22 and/or monitor 14. In addition to room cameras 146, a camera 152 may be disposed on a surgical light 154 within medical environment 10. Camera 152 may be configured to capture an image or a sequence of images of medical environment 10 and/or patient 12. Images captured by camera head 140, room cameras 146, and/or camera 152 may be routed to imaging system 108, which may then be displayed using touchscreen monitor 22, monitor 14, another display device, or a combination thereof. Additionally, the images captured by camera head 140, room cameras 146, and/or camera 152 may be provided to a database for storage (e.g., an EMR, or HIS).

Room cameras 146, camera 152, and/or camera head 140 (or another camera of imaging system 108) may include at least one solid state image sensor. For example, the image sensor of room cameras 146, camera 152, and/or camera head 140 may include a charge coupled device (CCD), a complementary metal-oxide semiconductor (CMOS) sensor, a charge-injection device (CID), or another suitable sensor technology. The image sensor of room cameras 146, camera 152, and/or camera head 140 may include a single image sensor. The single image sensor may be a grayscale image sensor or a color image sensor having an RGB color filter array deposited on its pixels. The image sensor of room cameras 146, camera 152, and/or camera head 140 may alternatively include three sensors: one sensor for detecting red light, one sensor for detecting green light, and one sensor for detecting blue light.

The medical procedure in which the images may be captured using room cameras 146, camera 152, and/or camera head 140 may be an exploratory procedure, a diagnostic procedure, a study, a surgical procedure, a non-surgical procedure, an invasive procedure, or a non-invasive procedure. As mentioned above, camera head 140 may be an endoscopic camera (e.g., coupled to endoscope 142). It is to be understood that the term endoscopic (and endoscopy in general) is not intended to be limiting, but rather camera head 140 may be configured to capture medical images from various scope-based procedures including but not limited to arthroscopy, ureteroscopy, laparoscopy, colonoscopy, bronchoscopy, etc.

Speakers 118 may be positioned within medical environment 10 to provide sounds, such as music, audible information, and/or alerts, that can be played within the medical environment during the medical procedure. For example, speaker(s) 118 may be installed on ceiling 150 and/or positioned on a bookshelf, a station, etc.

One or more microphones 16 may sample audio signals within medical environment 10.

The sampled audio signals may comprise the sounds played by speakers 118, noises from equipment within medical environment 10, and/or human speech (e.g., voice commands to control one or more medical devices, verbal information conveyed for documentation purposes, etc.). Microphone(s) 16 may be located within a speaker (e.g., a smart speaker) attached to monitor 14, as shown in FIG. 1A, and/or within the housing of touchscreen monitor 22. Microphones 16 may communicate via a wired and/or wireless connection with imaging system 108 and/or computing system 102. Microphones 16 may provide, record, and/or process the sampled audio signals. For example, as mentioned above, microphones 16 may determine and record the user's speech for documentation purposes (e.g., recording verbal information for educational purposes, making room calls, sending real-time information to pathologists, etc.). Additionally or alternatively, microphones 16 may be capable of processing the sampled audio signals, including recognizing the voice commands received from the user (e.g., surgeon, nurse, medical staff, etc.). The captured audio signal may also be processed using computing system 102.

Medical devices 120 may include one or more sensors, such as an image sensor, an audio sensor, a motion sensor, an optical sensor, or other types of sensors. These sensors may be configured to capture one or more images, one or more videos, audio, ambient light levels, or other data relating to a medical procedure being performed and/or medical environment 10 (where the medical procedure is being performed). Medical device 120 may be used to obtain or create images of patient 12 during a medical procedure from a variety of sources (e.g., from video cameras, video cassette recorders, X-ray scanners, which can convert X-ray films to digital files, digital X-ray acquisition apparatus, fluoroscopes, computed tomography (CT) scanners, magnetic resonance imaging (MRI) scanners, ultrasound scanners, charge-coupled (CCD) devices, and other types of scanners (handheld or otherwise)). For example, medical device 120 may capture images and/or videos of an anatomical structure of a patient (e.g., patient 12). As another example, medical device 120 may be a medical imaging device (e.g., MRI machines, CT machines, X-Ray machines, etc.). As yet another example, medical device 120 may be a biometric data capture device (e.g., blood pressure devices, pulse-ox devices, etc.).

As mentioned above, medical environment 10 may include one or more optical sensors 132. Optical sensors 132 may be disposed at various locations within medical environment 10. For example, optical sensors 132 may be located on walls 148 (e.g., proximate additional monitor 14), integrated within a wall plate 134 mounted to wall 148 or another surface of medical environment 10, on ceiling 150, or at other locations within medical environment 10. Optical sensors 132 may comprise ambient light sensors or another type of light sensor (e.g., photodiode, photoresistor, phototransistor, etc.) configured to measure an ambient light level in medical environment 10. Optical sensor 132 may measure an amount of incident light, which may indicate the ambient light level of medical environment 10.

Optical sensors 132 may be integrated in one or more and/or associated with encoder/decoder devices 700. Encoder/decoder devices 700 may be configured to transmit and/or receive data in a packetized format throughout medical environment 10. Encoder/decoder devices 700 may include light sources, which can create, or contribute to, light pollution. Encoder/decoder devices 700 may also include one or more of optical sensors 132. Encoder/decoder devices 700 may be affixed to walls 148, ceiling 150, floor 104, or other surfaces of medical environment 10. Furthermore, encoder/decoder devices 700 may be attached, coupled, and/or integrated into one or more devices within medical environment 10. For example, encoder/decoder device 700 may be coupled to monitor 14, medical device 120, or other devices within medical environment 10. Although FIG. 1A illustrates encoders/decoder devices 700, medical environment 10 can include additional, fewer, and/or any number r of encoder/decoder devices suitable for transmitting/receiving data throughout medical environment 10. Additionally, although FIG. 1A illustrates encoder/decoder devices 700, which may be capable of performing the functions of both an encoder device and a decoder device, persons of ordinary skill in the art will recognize that separate encoder devices and decoder devices may be disposed within medical environment 10 in addition to or instead of encoder/decoder devices 700. Additional details regarding encoder/decoder device 700 are described below with reference to FIG. 7.

Encoder/decoder devices 700 may be configured to encode/decode data representing images of the medical procedure being performed. For example, an encoder functionality of encoder/decoder device 700 device may encode data representing images captured using camera head 140 of endoscope 142, as shown in FIG. 1A. The encoded data may be transmitted by encoder/decoder device 700 (or a device associated with encoder/decoder device 700) to a monitor 14, touchscreen 22, or another display device. The encoded data may be decoded using a decoder functionality of encoder/decoder device 700. For example, encoder/decoder device 700 may be integrated in and/or associated with monitor 14, touchscreen 22, or another display device. As shown in FIG. 1A, encoder/decoder devices 700 may include one or more optical sensors 132. In addition to optical sensors 132, encoder/decoder devices 700 may include one or more light sources 130, which, as described above, may contribute light pollution within medical environment 10. Light emitted by light sources 130 can impact a measurement (e.g., an ambient light level measurement) by one or more optical sensors 132 in medical environment 10. To overcome this challenge, encoder/decoder devices 700 may be configured to change the state of one or more light sources 130 (e.g., turn the light source off) when corresponding optical sensor(s) 132 are being used to measure an ambient light level of medical environment 10. After light sources 130 are off, the optical sensors 132 may measure the ambient light level and provide the measured ambient light level to computing system 102 to determine whether a setting of one or more corresponding light sources 130 should be adjusted. Once the measurement has been made, the state of the corresponding light source 130 may be changed (e.g., the light source may be turned back on). Ambient light level measurements may be performed periodically (e.g., every second, every 5 seconds, every minute, etc.), and/or based on a user input (e.g., input from a surgeon, medical staff, etc.). For example, a user may select an option to measure an ambient light level of medical environment 10. The option may be presented within a user interface rendered on a display device (e.g., touchscreen 22). Additionally or alternatively, the option may be invoked by the user engaging with a physical button/switch, uttering a voice command, etc.

Medical environment 10 may include one or more instances of light source 130. Light sources 130 may vary in shape, size, function, light profile, or other aspects. For example, light sources 130 may be light emitting diodes (LEDs), incandescent lamps, halogen lights, discharge tubes, other types of lights, and/or combinations thereof. Non-limiting examples of light sources 130 and the locations of light sources 130 are presented in FIG. 1A. In addition to light sources 130 described above, light sources may include additional monitor 14, touchscreen monitor 22, surgical light 154, display devices of medical device 120, overhead light 95, and/or other devices within medical environment 10 that emit light. Light sources 130 may include light sources located on portable cart 106, surgical table 17, room cameras 146, medical device 120, additional monitor 14, encoders/decoder devices 700, walls 148 (e.g., power outlets, suction lines, etc.), ceiling 150 (e.g., as part of an intercom, fire alarm, emergency signal, etc.), and/or at other locations within medical environment 10.

Figure 1B:
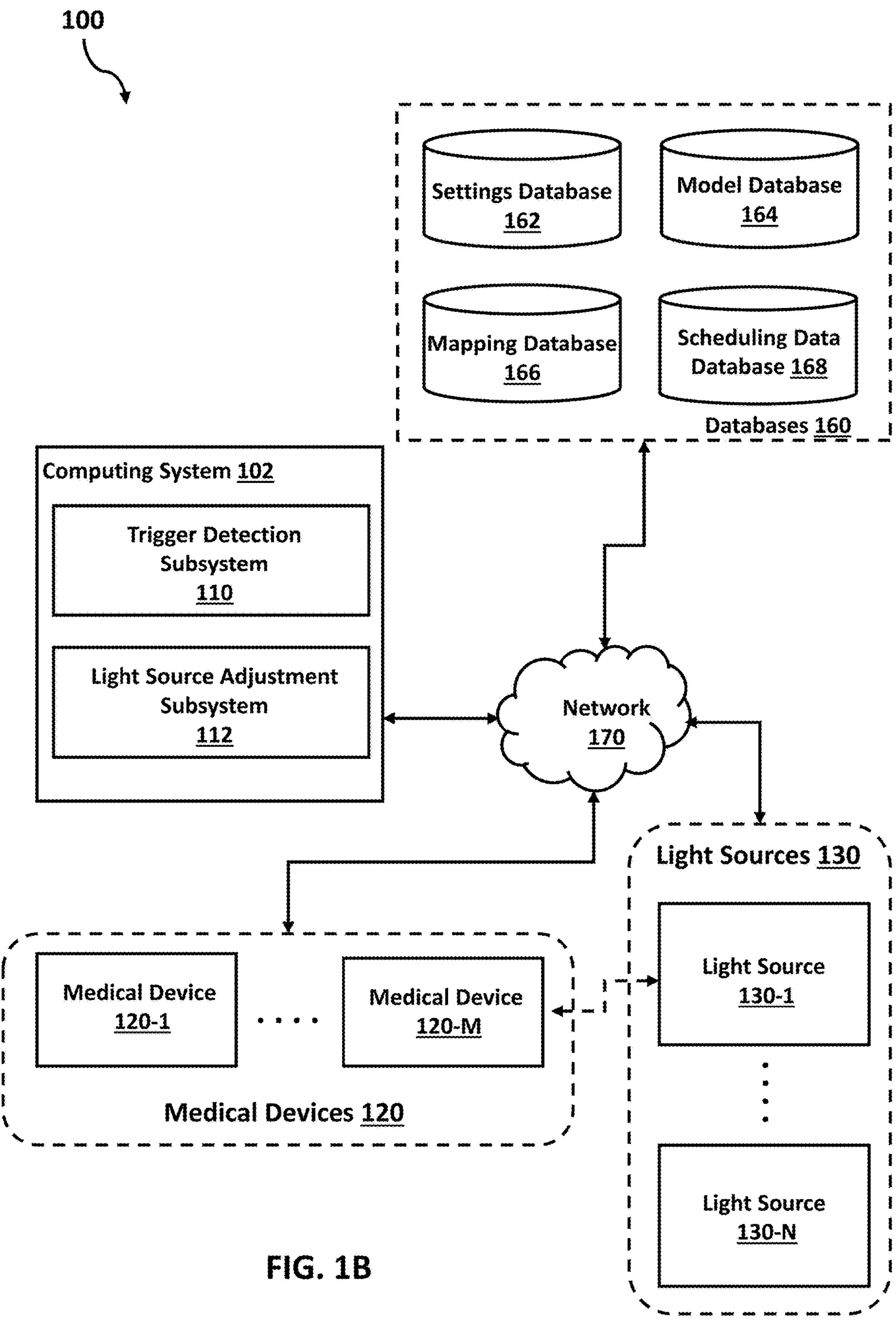
FIG. 1B illustrates an example system for reducing light pollution within a medical environment, according to some aspects.

FIG. 1B illustrates an example system for reducing light pollution within a medical environment, according to some aspects. System 100 may include computing system 102, medical devices 120 (e.g., medical devices 120-1 to 120-M), light sources 130 (e.g., light sources 130-1 to 130-N), databases 160 (e.g., settings database 162, model database 164, mapping database 166, scheduling data database 168), or other components. Components of system 100 may communicate with one another using network 170 (e.g., a local area network (LAN), the Internet, etc.).

As mentioned above, medical devices 120 may include one or more sensors, such as an image sensor, an audio sensor, an optical sensor, a motion sensor, or other types of sensors. For example, with reference to FIG. 1A, medical device 120 may be an endoscope 142. Endoscope 142 may include a camera head 140 having one or more image sensors. Medical device 120 may be used to obtain or create images of patient 12 during a medical procedure from a variety of sources (e.g., from video cameras, video cassette recorders, X-ray scanners (which can convert X-ray films to digital files), digital X-ray acquisition apparatus, fluoroscopes, computed tomography (CT) scanners, magnetic resonance imaging (MRI) scanners, ultrasound scanners, charge-coupled (CCD) devices, and/or other types of scanners (handheld or otherwise)). For example, medical device 120 may capture images and/or videos depicting an anatomical structure of patient 12, as seen with respect to FIG. 1A. As another example, medical device 120 may be a medical imaging device (e.g., MRI machines, CT machines, X-Ray machines, etc.). As another example, medical device 120 may be a biometric data capture device (e.g., a blood pressure device, pulse-ox device, etc.).

Medical devices 120 may include one or more light sources, such as light sources 130 shown in FIG. 1A (which are described in greater detail below). For example, camera head 140 may include a light source. This light source may emit light of a particular color (e.g., red) that may or may not blink when camera head 140 is being used. For simplicity, light sources 130 are illustrated separately from medical devices 120. However, persons of ordinary skill in the art will recognize that some of medical devices 120 of FIG. 1B may include or be coupled to light sources 130, as indicated by the dashed arrows.

Light sources 130-1 to 130-N (collectively referred to herein as "light sources 130" and individually as "light source 130") may be disposed throughout medical environment 10 at various locations. For example, light sources 130 may be included on room camera 146, surgical table 17, medical devices 120, and/or at other locations. In one example, light sources 130 may be included within wall plate 134 on wall 148 and/or mounted to ceiling 150. Light sources 130 may also instead or additionally be integrated within other devices located in medical environment 10 (shown in FIG. 1A) not explicitly described herein.

The arrangement of light sources 130 may be stored in mapping database 166. For example, mapping database 166 may indicate a location of each light source 130 within medical environment 10 (shown in FIG. 1A), an identifier for identifying notifications received from light source 130 and/or sending instructions to light source 130, or other information. Mapping database 166 may store information indicating which light sources 130 are proximate to a particular light source (e.g., which may contribute to light pollution detected in medical environment 10). The number of light sources 130 may vary based on medical environment 10, a type of medical procedure being performed within medical environment 10, users associated with the medical procedure (e.g., a surgeon, medical staff, etc.), or other criteria.

Medical devices 120 and/or light sources 130 may be capable of communicating with one or more components of system 100 via network 170 and/or via a direct (e.g., wired) connection. For example, medical device 120 may connect to various components of system 100 to cause one or more actions to be performed. In an example, medical device 120, light source 130, or another component of system 100 may include a device used to display images and/or videos to a user (e.g., a surgeon, medical staff, etc.). Examples of medical devices 120 and/or light sources 130 that may display images and/or videos may include but are not limited to desktop computers, servers, mobile computers, smart devices, wearable devices, cloud computing platforms, display devices, or other client devices. For example, images and/or video may be displayed using monitor 14 and/or touchscreen 22 of FIG. 1A. Medical device 120 and/or light source 130 may include computing hardware, such as one or more processors, memory, communications components, display components, audio capture/output devices, image capture/output components, other components, and/or combinations thereof.

It should be noted that, while one or more operations are described herein as being performed by particular components of computing system 102, those operations may be performed by other components of computing system 102 or other components of system 100. As an example, while one or more operations are described herein as being performed by components of computing system 102, those operations may alternatively be performed by one or more of medical devices 120 and/or light sources 130.

As illustrated in FIG. 1B, computing system 102 may include one or more subsystems. For example, computing system 102 may include a trigger detection subsystem 110, a light source adjustment subsystem 112, or other subsystems. Subsystems 110-112 may be implemented using one or more processors, memory, and/or interfaces. Distributed computing architectures and/or cloud-based computing architectures may alternatively or additionally be used to implement some or all of the functionalities associated with subsystems 110-112.

Trigger detection subsystem 110 may be configured to detect one or more triggers indicating that a light source is to be adjusted for use during a medical procedure. For example, the triggers may indicate that a light source 130 is to be placed into a medical procedure mode. Placing light source 130 into the medical procedure mode may include causing a setting of light source 130 to be adjusted to a predefined setting. This predefined setting may be stored within settings database 162. The predefined setting may indicate a predefined color, intensity, blink rate, or other characteristic of light emitted by light source 130. For example, the predefined setting for light source 130 may comprise adjusting the light source to emit white light at a particular intensity (e.g., 20% of maximum luminosity) with a constant blink rate. The predefined settings stored in settings database 162 may indicate the light profile (or light profiles) for adjusting each of light sources 130.

Figure 2:
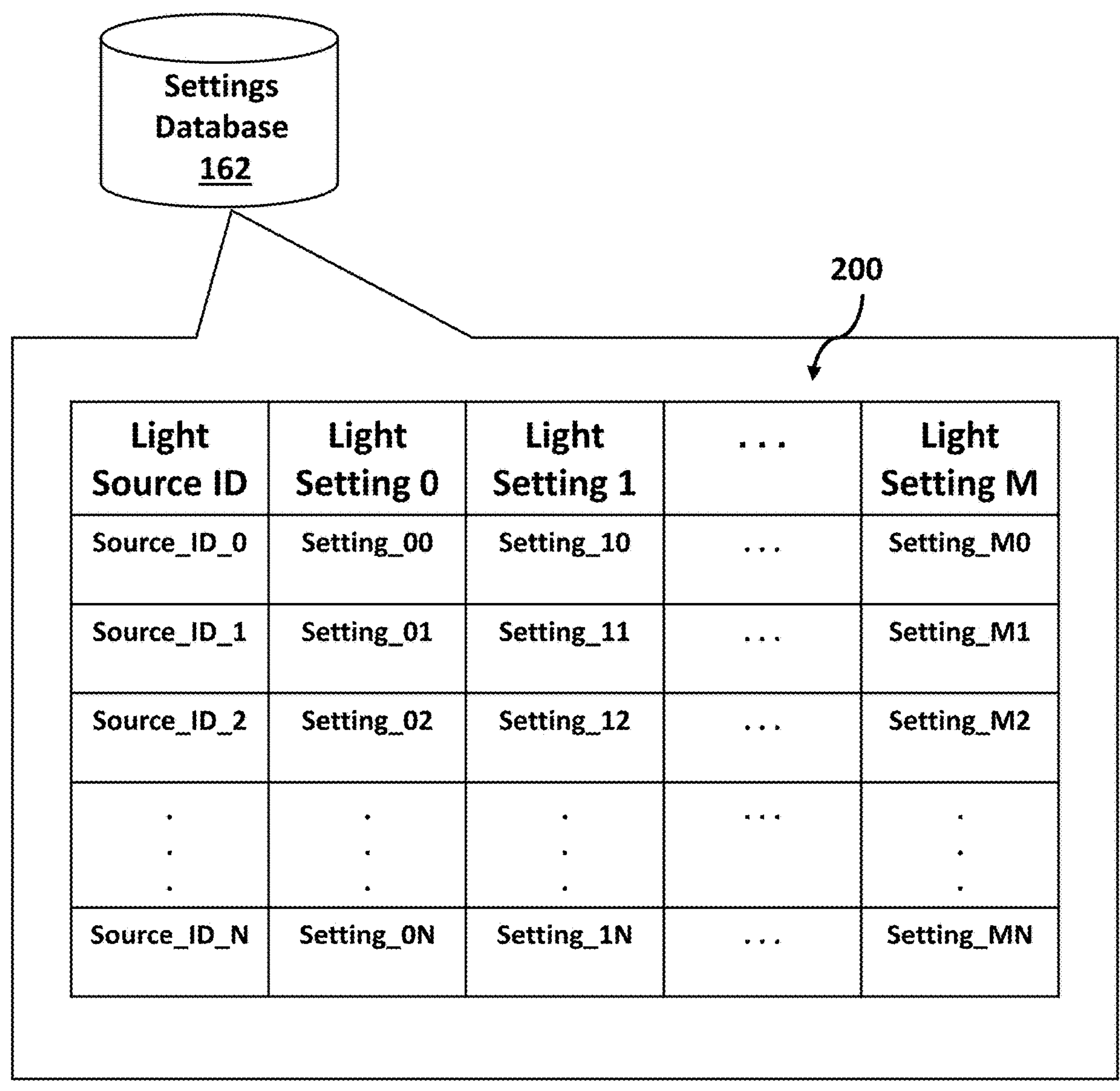
FIG. 2 illustrates an example settings database, according to some aspects.

As an example, with reference to FIG. 2, settings database 162 may store data structure 200 including a list of light sources (e.g., corresponding with each of light sources 130 shown in FIGS. 1A-1B), as well as one or more predefined light settings for the light sources. For example, each of light sources 130 may be represented by a respective row within data structure 200. In data structure 200, light sources 130 located within medical environment 10 may be identified using a light source identifier (ID). As illustrated by data structure 200, light sources 130 may be represented by light source identifiers including "Source_ID_0" through "Source_ID_N," where N represents a total number of light sources 130 within medical environment 10.

Additional light sources may be added to medical environment 10, and thus corresponding entries may be added to data structure 200. The new entry may be an additional row added to data structure 200. Furthermore, existing light sources may be removed from medical environment 10, and thus corresponding entries may be removed and/or masked in data structure 200.

As shown in FIG. 2, some light sources may include multiple predefined settings. Each of the predefined settings may be associated with a different type of medical procedure, different user(s) (e.g., a surgeon, medical staff, etc.), or other criteria. In the example shown in FIG. 2, settings database 162 may store light settings Setting_00 through Setting_M0 for one of light sources 130 assigned the light source ID "Source_ID_0." Each of Setting_00 through Setting_M0 may comprise different predefined settings. Similarly, as another example, settings database 162 may store light settings Setting_0N through Setting_MN for another one of light sources 130 assigned the light source ID "Source_ID_N." Each of Setting_0N through Setting_MN may comprise different predefined settings. Additional light settings may be added to data structure 200 as a new column. For example, a new light setting associated with the one of light sources 130 assigned the light source ID "Source_ID_0" may cause an additional column to be added to data structure 200, to store the new light setting. Additionally or alternatively, changes to existing light settings may also be made, such as removing and/or masking a light setting of one or more of light sources 130.

The different settings included in data structure 200 stored in settings database 162 may be for different users (e.g., surgeons, medical staff, etc.). Different users may have different lighting condition preferences. For example, a particular predefined setting may be selected for one of light sources 130 based on preferences of a user associated with the medical procedure (e.g., a surgeon, medical staff, etc.). Users may indicate which predefined settings they prefer for light sources 130 for different medical procedures. For example, one light source may emit white light at 70% of maximum luminosity for one surgeon performing a medical procedure, while that same light source may emit light at 50% of maximum luminosity for another surgeon performing the same medical procedure.

Adjustments may be made to the predefined settings. For example, after being adjusted to the predefined setting, a setting of a light source 130 may be further adjusted. The further adjustments to the setting of light source 130 may be updated in settings database 162 (shown in FIG. 1B). For example, if the blink rate and/or light intensity of light source 130 is determined to be distracting or bothersome after being adjusted to the predefined setting, then the blink rate and/or light intensity may subsequently be adjusted by a user (e.g., surgeon, medical staff, etc.), and the updated settings may be stored (e.g., in data structure 200 in FIG. 2). After the setting of light source 130 has been further adjusted, an ambient light level of medical environment may be determined. The updated ambient light level may also be stored in settings database 162. Light emitted by one or more other light sources 130 may be adjusted for use during the medical procedure based on the updated ambient light level of light source 130. Thus, for a subsequent medical procedure, the light source's setting may be adjusted to the updated setting.

Figure 3:
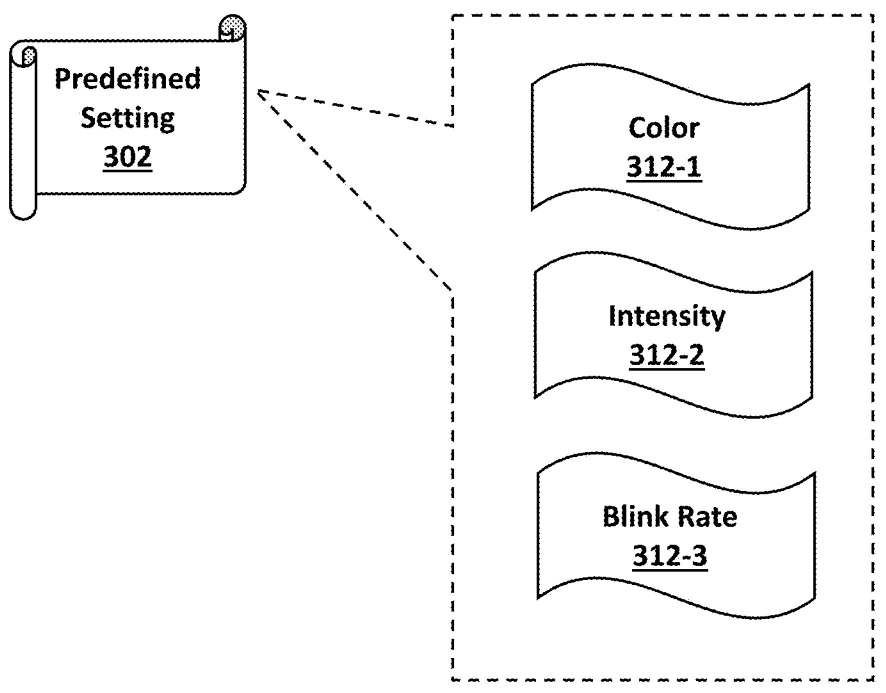
FIG. 3 illustrates an example predefined setting, according to some aspects.

FIG. 3 illustrates an example predefined setting 302 for a light source 130, according to some aspects. Predefined setting 302 may include one or more parameter values for light source 130 when used for a medical procedure. In FIG. 3, predefined setting 302 may represent one of the light settings stored by data structure 200 (shown in FIG. 2). For example, predefined setting 302 may represent Setting_00, Setting_MN, or another setting. Predefined setting 302 may include individual settings for various aspects of light to be emitted by light source 130. For example, predefined setting 302 may indicate a color 312-1 of the light to be emitted by light source 130, an intensity 312-2 of the light to be emitted by light source 130, a blink rate 312-3 of the light to be emitted by light source 130, or other characteristics.

Color 312-1 may indicate a color of light to be emitted by light source 130 (e.g., during a medical procedure). Different colors of light emitted by light source 130 may increase the visibility of a surgical video feed displayed on a display device (e.g., additional monitor 14 and/or touchscreen 22 of FIG. 1A), at least because the light may be emitted towards the display device. For example, green light may minimally impact visibility of images on a display screen, and white light may decrease contrast of the display screen. Some colors of light may distract users within the medical environment. For example, red light may be more distracting to users than white light in a medical environment. Different colored lights may be used for different devices, to indicate different events, or for other purposes. Some example colors for the emitted light may include but are not limited to white, red, green, blue, or other colors.

Intensity 312-2 may indicate an intensity of light to be emitted by light source 130 (e.g., during a medical procedure). For example, during the medical procedure, light source 130 may emit light at a lowered intensity to avoid distracting medical staff. The lowered intensity of emitted light may instead or additionally improve the visibility of a surgical video feed displayed on a display (e.g., by reducing glare on the display). Further still, the lowered intensity of emitted light may reduce alarm fatigue in users (e.g., surgeons, medical staff, etc.). During medical procedures, light sources 130 (shown in FIG. 1A) may be configured to emit light at a lower intensity than when medical procedures are not being performed. For example, during a medical procedure, light may be emitted at a percentage of a maximum luminosity of light source 130 (e.g., 5% or less of maximum luminosity, 10% or less of maximum luminosity, 20% or less of maximum luminosity, 50% or less of maximum luminosity, or other values). As another example, no light may be emitted from light source 130 during the medical procedure. In this example, the setting of light source 130 may be adjusted to 0%, or approximately 0% (e.g., less than 1%, less than 2%, etc.) of the maximum luminosity. Reducing the intensity of light emitted by light source 130 may reduce light pollution in the medical environment, which may increase contrast and clarity and reduce the glare of a surgical video feed displayed on a display device.

Blink rate 312-3 may indicate a frequency with which light source 130 may blink (i.e., alternating between an on state and an off state). Different blink rates may be used to convey different information in the medical environment. For example, faster blink rates (e.g., higher frequency) may be associated with emergencies, whereas slower blink rates (e.g., lower frequency) may indicate a condition of patient 12 and/or medical environment 10 (shown in FIG. 1A) is stable. Blinking lights in the medical environment may distract medical staff. Therefore, adjusting the blink rate or otherwise causing a light to no longer blink may minimize distractions within medical environment 10 (shown in FIG. 1A).

Predefined setting 302 may also include default settings. A default setting refers to a setting for light source 130 used during times other than when the medical procedure is being performed. For example, after the medical procedure has been completed, light sources 130 may be adjusted to their respective default settings. Default settings may include particular colors of light, intensities of the light, blink rates, or other characteristics of the emitted light. In the default setting, for example, the colors of light emitted may include white, blue, yellow, red, green, or other colors. As another example, the intensities of the light for the default setting may include greater than or equal to 60%, 75%, 80%, 85%, or 90% of maximum luminosity. As yet another example, the blink rates for the default setting may include no blinking or blinking at a particular frequency in which the light will oscillate between a first intensity and a second intensity. Example frequencies may include 60 Hz, 120 Hz, 200 Hz, or other frequencies.

Returning to FIG. 1B, trigger detection subsystem 110 may be configured to determine when a setting of a light source 130 within medical environment 10 (shown in FIG. 1A) is to be adjusted for use during a medical procedure. As mentioned above, during medical procedures (e.g., endoscopic surgical procedures), minimal light pollution may be desired. Light pollution may reduce visibility and clarity of, and increase glare on, medical images associated with the medical procedure that are displayed on a display. Moreover, light sources 130 within medical environment 10 may distract users, and in some instances cause "alarm fatigue." Alarm fatigue may occur when users (e.g., surgeons, medical staff, etc.) continually notice the light emitted by light sources 130 and believe the light sources 130 are trying to notify them of an emergency, when in reality, no emergency is occurring.

Trigger detection subsystem 110 may be configured to determine and/or continually monitor settings of one or more of light sources 130. For example, trigger detection subsystem 110 may determine a current setting of some or all of light sources 130 at a particular cadence (e.g., every second, every 30 seconds, every minute, etc.). Optionally, the settings of some or all of light sources 130 may be tracked and stored in memory to identify changes in the settings over a certain time period (e.g., over a day, over a week, etc.).

Based on a determination that a medical procedure is being performed, or is about to be performed, some or all of light sources 130 may be adjusted. A trigger may indicate when the medical procedure is being performed or is about to begin. Some triggers may be automatic such that little to no human intervention may be needed to initiate the adjustment of a setting of one or more light sources. On the other hand, some triggers may include human actions. For example, a trigger may be a manual selection by a user to place one or more of light sources 130 into a mode for use during a medical procedure. One or more of light sources 130 may include a manual control mechanism, such as a switch, toggle, slide, button, or other user input device. Actuation of the manual control mechanism may cause light sources 130 to be placed in a mode for use during the medical procedure.

Figure 4A:
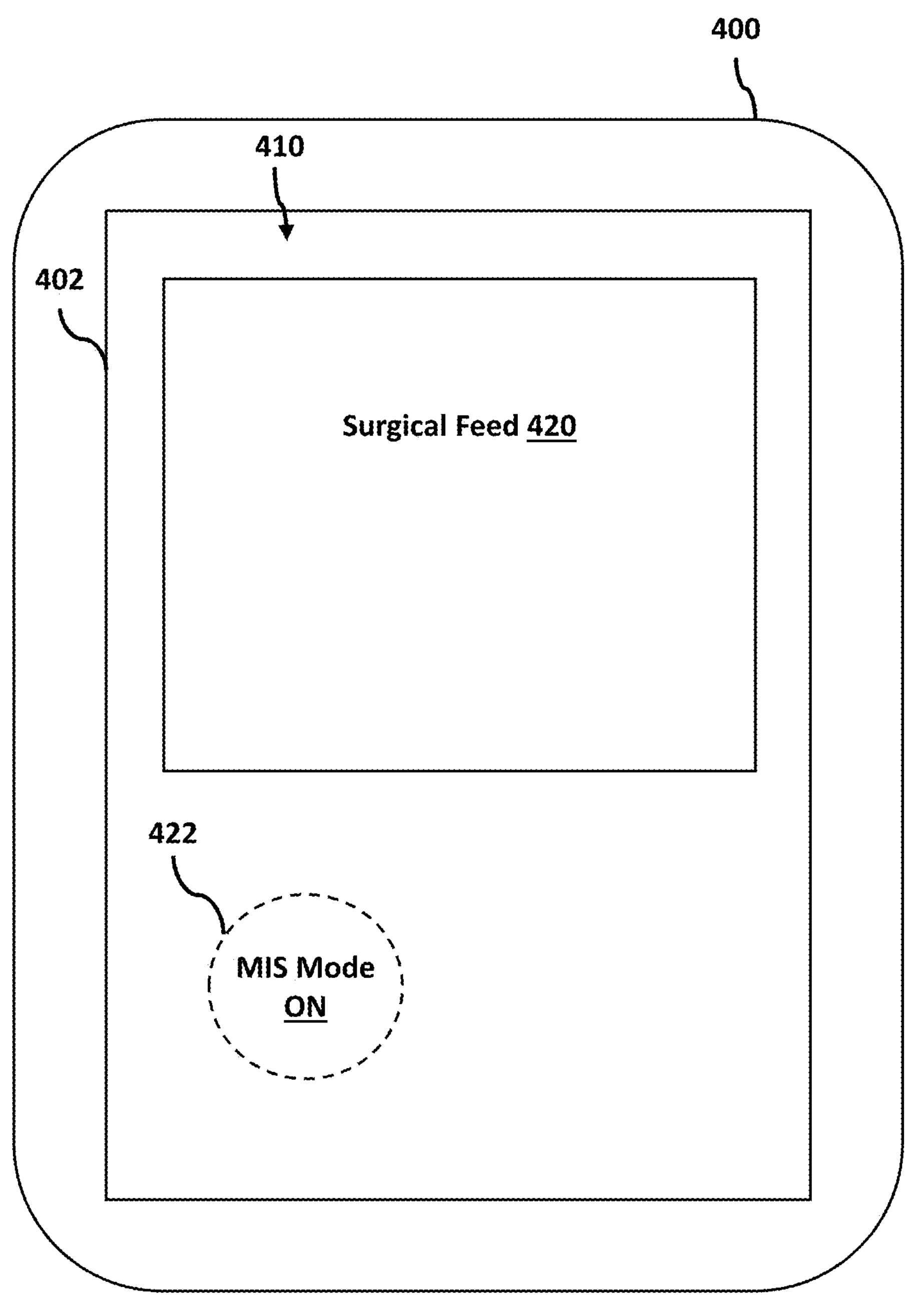
FIG. 4A illustrates an example user device displaying a surgical video feed, according to some aspects.

An option for light adjustment may be presented within a user interface displayed using monitor 14 and/or touchscreen 22 of FIG. 1A to a user (e.g., surgeon, medical staff, etc.). The presented option may cause one or more of light sources 130 to be adjusted for use during the medical procedure. For example, with reference to FIG. 4A, a user device 400 (e.g., a client device, medical device 120, etc.) may render a user interface (UI) 410 on a display 402. Display 402 may be a touchscreen. UI 410 may present content to users (e.g., a surgeon, medical staff, etc.) within medical environment 10 of FIG. 1A. For example, the content may include a surgical video feed 420 including one or more images of a medical procedure (e.g., a surgical procedure) captured by camera head 140. The images may be presented within UI 410 to aid the user during a medical procedure. UI 410 may also display a graphical indicator 422. User device 400 may be programmed to detect when graphical indicator 422 has been selected by the user. User device 400 may be programmed to cause a setting of one or more of light sources 130 to be adjusted to a predefined setting based on graphical indicator 422 being selected. UI 410 may display one or more graphical indicators, each indicator corresponding to a light source of light sources 130. Using the graphical indicators 422, the user may be able to select how the settings of each of light sources 130 are to be adjusted.

Trigger detection subsystem 110 may receive the selection indicating which of light sources 130 should be adjusted, as well as optionally what adjustments should be made to a setting of light sources 130. Trigger detection subsystem 110 may, for example, be communicably coupled to user device 400. For example, user device 400 may connect to computing system 102 via network 170 illustrated in FIG. 1A. In some examples, display 402 of user device 400 may represent one instance of light sources 130.

Trigger detection subsystem 110 may determine which light sources 130 are to be adjusted, as well as the setting with which light sources 130 are to be adjusted to, based on the selection via user device 400. Trigger detection subsystem 110 may send a notification to light sources 130 indicating that the light sources 130 are to be adjusted. Optionally, the notification may instead or additionally indicate the setting that the light sources 130 are to be adjusted to.

Trigger detection subsystem 110 may be configured to determine that a light source 130 is to be adjusted (e.g., placed into the medical procedure mode) based on a setting of one or more medical lights within the medical environment being adjusted during the medical procedure. As an example, as shown in FIG. 1A, surgical light 154 of medical environment 10 may be configured to emit light for illuminating one or more regions of patient 12 and/or medical environment 10 where the medical procedure is being performed. The intensity, color, field of illumination (e.g., spot size), location (e.g., where the light is directed), or other characteristics of the emitted light may be adjustable depending on the particular activities being performed in a medical procedure. Surgical light 154 and/or overhead light 95, or other medical lights within medical environment 10 (e.g., lamps, flashlights, etc.) may have multiple settings that they can be placed in. Each setting may be associated with a different intensity, color, field of illumination, location, etc. For example, one setting may cause surgical light 154 and/or overhead light 95 to emit white light at a predefined intensity level (e.g., greater than or equal to 50%, 75%, 100%, etc., of maximum luminosity). This example setting may be associated with pre-medical procedure activities. As another example, one setting may cause surgical light 154 and/or overhead light 95 to emit green light. The green light may be emitted at a predefined intensity level (e.g., greater than or equal to 50%, 75%, 100%, etc. of maximum intensity). This example setting may be associated with medical procedure activities. Different colored light (e.g., red, yellow, green, blue, violet, etc.) may instead or additionally be emitted from other light sources 130 within medical environment 10. Light sources 130 may be configured to emit light in one or more colors.

Trigger detection subsystem 110 may detect that a setting of surgical light 154 or another medical light has been adjusted. For example, trigger detection subsystem 110 may determine that a setting of surgical light 154 has been adjusted. Trigger detection subsystem 110 may further identify the setting that surgical light 154 has been adjusted to. If trigger detection subsystem 110 determines that surgical light 154 has been adjusted to a setting associated with the medical procedure beginning (or a particular phase of the medical procedure), one or more light sources 130 may also be adjusted. For example, trigger detection subsystem 110 may determine that a setting of surgical light 154 has been adjusted such that surgical light 154 emits green light at 20% of maximum luminosity. Adjusting a setting of surgical light 154 to emit green light (e.g., green light at 20% of maximum luminosity) may indicate that one or more of light sources 130 should also be adjusted to a predefined setting for use during the medical procedure. As another example, trigger detection subsystem 110 may determine that a setting of surgical light 154 has been adjusted such that surgical light 154 emits white light at 10% of maximum luminosity. Adjusting a setting of surgical light 154 to emit white light (e.g., white light at 5% or 10% of maximum luminosity) may indicate that one or more of light sources 130 should also be adjusted to a predefined setting for use during the medical procedure.

Trigger detection subsystem 110 may be configured to detect a trigger to adjust a setting of one or more of light sources 130 for use during a medical procedure based on an ambient light level of medical environment 10. As mentioned above with reference to FIG. 1A, medical environment 10 may include one or more optical sensors 132. Optical sensor 132 may be configured to measure an ambient light level of medical environment 10. For example, optical sensor 132 may be a photodiode, a photoresistor, a phototransistor, or another type of optical sensor. Optical sensor 132 may be included within one or more devices in medical environment 10, such as additional monitor 14. In one example, optical sensor 132 may be embedded within walls 148 (e.g., within wall plate 134) and/or ceiling 150. Optical sensor 132 may be configured to measure an amount of incident light to determine the ambient light level of medical environment 10.

Trigger detection subsystem 110 may be configured to receive a measurement of a current ambient light level within medical environment 10 from optical sensor 132. The measurement of the current ambient light level may be compared to a threshold ambient light level. For example, trigger detection subsystem 110 may be configured to determine whether the current ambient light level of medical environment 10 is less than or equal to a threshold ambient light level. If it is determined that the current ambient light level is less than or equal to the threshold ambient light level, it may be determined that medical environment 10 is being used, or is about to be used, to perform the medical procedure. Accordingly, trigger detection subsystem 110 may notify light source adjustment subsystem 112 that a setting of one or more of light sources 130 is to be adjusted for use during the medical procedure. Light source adjustment subsystem 112, as described in greater detail below, may cause a setting of each light source 130 to be adjusted to a predefined setting.

Trigger detection subsystem 110 may be configured to measure/estimate a current ambient light level within medical environment 10 based on images captured by room cameras 146 and camera 152 disposed on surgical light 154. One or more machine learning models may be used to measure the ambient light level within medical environment 10 using images captured by room cameras 146. As an example, trigger detection subsystem 110 may receive images of medical environment 10, input the images to one or more machine learning models that estimate an ambient light level and, optionally, determine whether the estimated ambient light level is less than or equal to a threshold ambient light level. If the estimated ambient light level is determined to be less than or equal to the threshold ambient light level, then the one or more machine learning models may output a result indicating that a setting of one or more of light sources 130 are to be adjusted for use during the medical procedure. Trigger detection subsystem 110 may notify light source adjustment subsystem 112 that the setting of the one or more of light sources 130 are to be adjusted for use during the medical procedure based on the output result.

Trigger detection subsystem 110 may determine a predefined setting with which to adjust the one or more of light sources 130 based on the ambient light level. Trigger detection subsystem 110 may retrieve a predefined setting for light source 130 from settings database 162 based on the ambient light level. For example, lower ambient light levels may indicate that light source 130 is to be adjusted to a first predefined setting. As another example, higher ambient light levels may indicate that light source 130 should be adjusted to a second predefined setting.

Trigger detection subsystem 110 may be configured to detect light emitted by one or more other light sources 130 within the medical environment. If the light emitted by the one or more other light sources 130 has been adjusted to a predefined setting associated with the medical procedure being performed, it may be determined that the setting of another light source 130 should also be adjusted to the predefined setting.

Figure 4B:
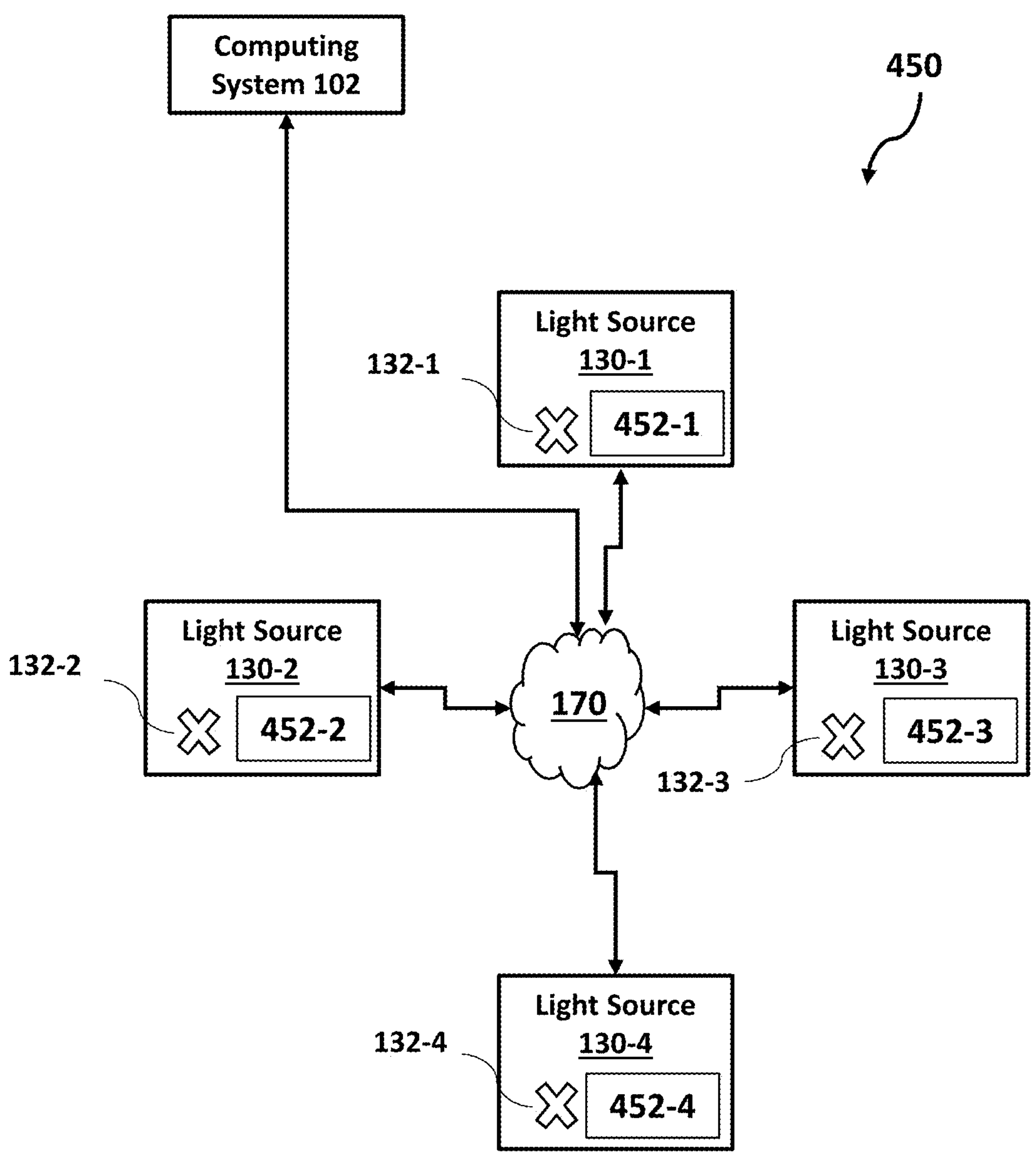
FIG. 4B illustrates an example block diagram of one or more light sources within a medical environment, according to some aspects.

With reference to FIG. 4B, system 450 may represent a simplified block diagram of light sources 130 and computing system 102. Although only four instances of light source 130 are illustrated in FIG. 4B, it is to be understood that additional or fewer light sources may be included. In system 450, computing system 102 may be configured to communicate with light sources 130-1, 130-2, 130-3, and 130-4 (collectively light sources 130) via network 170. Alternatively or additionally, each of light sources 130 may communicate directly with one another or directly with computing system 102 (e.g., via wired and/or wireless communication).

Light sources 130 may each include one or more optical sensors and one or more controllers. For example, light source 130-1 may include optical sensor 132-1 and controller 452-1, light source 130-2 may include optical sensor 132-2 and controller 452-2, light source 130-3 may include optical sensor 132-3 and controller 452-3, and light source 130-4 may include optical sensor 132-4 and controller 452-4. Although one sensor and one controller are included in each light source, persons of ordinary skill in the art will recognize that additional or fewer sensors and/or controllers may be included. Additionally, for simplicity, each of the sensors, controllers, and light sources may be the same or similar.

Optical sensors 132 may be configured to measure an ambient light level of medical environment 10. Optical sensors 132 may communicate the measured ambient light level to computing system 102 via network 170. Computing system 102 (e.g., via trigger detection subsystem 110) may determine whether the measured ambient light level is associated with a medical procedure being performed. If it is determined that the measured ambient light level is associated with a medical procedure being performed, computing system 102 may cause some or all of light sources 130 to adjust their setting to a predefined setting associated with light sources 130 being used during the medical procedure.

In an example, optical sensor 132-1 of light source 130-1 may detect an ambient light level within medical environment 10 (shown in FIG. 1A) based on light emitted from light sources 130-2, 130-3, and 130-4. The detected ambient light level may be provided to computing system 102 via controller 452-1 of light source 130-1. Computing system 102 may determine, based on the detected ambient light level, whether a setting of light source 130-1 should be adjusted to a predefined setting. In some examples, controller 452-1 of light source 130-1 may additionally or alternatively determine whether a setting of light source 130-1 should be adjusted to the predefined setting. If computing system 102 determines that the detected ambient light level is less than or equal to a predefined threshold ambient light level, it may be determined that the setting of light source 130-1 should be adjusted (e.g., to place it in the medical procedure mode). For example, optical sensor 132-1 may measure the ambient light level to be ambient light level 1 (e.g., "AL1"). Controller 452-1 may provide the measured ambient light level (AL1) to computing system 102. Computing system 102 may compare the measured ambient light level (AL1) to a threshold ambient light level (e.g., "TAL"). Computing system 102 may determine, based on the comparison, whether the measured ambient light level (AL1) is less than or equal to the predefined threshold light level (TAL, e.g., AL1≤TAL). If it is determined that AL1 is less than or equal to TAL, computing system 102 may cause the setting of light source 130-1 to be adjusted. For example, computing system 102 may provide instructions to controller 452-1 to cause light source 130-1 to emit light in accordance with the predefined setting.

Computing system 102 and/or controllers 452 may determine a setting of one or more of light sources 130. For example, controllers 452 may poll a current setting of their respective light source 130. The current setting may be provided to computing system 102, which may be used to determine whether the setting of light sources 130 should be adjusted. The setting of light sources 130 may be continually monitored. For example, controllers 452 may provide the current setting of light sources 130 to trigger detection subsystem 110, which may determine a current setting of some or all of light sources 130 at a particular cadence (e.g., every second, every 30 seconds, every minute, etc.). Optionally, the settings of some or all of light sources 130 may be tracked and stored in memory to identify changes in settings over a certain time period (e.g., over a day, over a week, etc.). For example, each of light sources 130 may include memory that may store the determined setting, along with temporal data indicating when light sources 130 emitted light in accordance with that setting. As another example, the determined setting of light sources 130 may be provided to computing system 102, which may store the determined settings in memory.

Computing system 102 may be configured to designate one or more of optical sensors 132 for use in detecting an ambient light level of medical environment 10 (shown in FIG. 1A). For example, with reference to FIG. 4B, computing system 102 may designate optical sensor 132-1 of light source 130-1 for measuring an ambient light level of medical environment 10. One of optical sensors 132 may be designated to measure the ambient light level based on the light source 130 associated with that optical sensor 132, a current setting of the optical sensor 132, a user selection of the optical sensor 132, a proximity of the optical sensor 132 to monitor 14, touchscreen 22, endoscope 142, surgical table 17, and/or surgical light 154, and/or a combination thereof. A controller 452 associated with a same one of light sources 130 that includes the designated optical sensor 132 may be configured to provide the measured ambient light level to computing system 102, which may determine whether a setting of one or more of light sources 130 in medical environment 10 should be adjusted for use during a medical procedure. The same controller 452 may alternatively provide instructions directly to one or more of light sources 130 to cause the light sources 130 to adjust their setting to a predefined setting associated with the medical procedure.

Optical sensors 132 may be integrated in and/or associated with one or more of encoder/decoder devices 700. As mentioned above, encoder/decoder devices 700 may be configured to encode and/or decode data representing images of the medical procedure being performed. For example, an encoder functionality of encoder/decoder device 700 may be configured to encode data representing images captured using camera head 140 of endoscope 142, as shown in FIG. 1A. The encoded data may be transmitted by encoder/decoder device 700 (or a device associated with the encoder) to monitor 14, touchscreen 22, or another display device. The encoded data may be decoded using a decoder functionality encoder/decoder device 700 integrated into monitor 14, touchscreen 22, or another display device. In addition to optical sensors 132, encoder/decoder devices 700 may include one or more light sources 130. As mentioned above, light sources 130 may contribute light pollution within medical environment 10. Moreover, light emitted by light sources 130 can impact a measurement by a corresponding one of optical sensors 132 of an ambient light level of medical environment 10. To overcome this challenge, encoder/decoder devices 700 may be configured to change the state of one of light sources 130 (e.g., turn the light source off) when a corresponding one of optical sensors 132 is being used to measure an ambient light level of medical environment 10. The optical sensor 132 may measure the ambient light level and provide the measured ambient light level to computing system 102. Computing system 102 may determine whether a setting of one or more of light sources 130 should be adjusted. After optical sensor 132 has completed the measurement, the state of the corresponding light source 130 may again be changed (e.g., the light source may be turned back on). The measurements may be performed periodically (e.g., every second, every 5 seconds, every minute, etc.). The measurements may instead or additionally be performed based on an input from a user (e.g., surgeon, medical staff, etc.). For example, a user may select an option to measure an ambient light level of medical environment 10. The option may be presented within a user interface rendered on touchscreen 22. Additionally or alternatively, the option may be invoked by the user engaging with a physical button and/or switch, uttering a voice command, etc.

Computing system 102 and/or controllers 452 may be configured to cause a setting of a light source to be adjusted based on a determination made using ambient light levels measured by some or all of optical sensors 132. For example, optical sensor 132-1 may measure an ambient light level based on light emitted by light source 130-2, light source 130-3, and/or light source 130-4. Controller 452-1 of light source 130-1 may be configured to determine whether the measured ambient light level is less than or equal to a threshold light level (e.g., thereby indicating that the medical procedure is being performed). Controller 452-1 of light source 130-1 may be configured to provide the measured ambient light level to computing system 102, which may instead or additionally determine whether the measured ambient light level is less than or equal to the threshold light level. Based on the measured ambient light level being less than the threshold ambient light level, it may be determined that a setting of one or more of light source 130-2, light source 130-3, and/or light source 130-4 has been adjusted for use during a medical procedure. If controller 452-1 and/or computing system 102 determine that the measured ambient light level is less than or equal to the threshold ambient light level, then controller 452-1 may cause a setting of light source 130-1 to be adjusted to a predefined setting. For example, computing system 102 and/or controller 452-1 may access data structure 200 stored in settings database 162 to identify a light source ID and one or more light settings (e.g., light settings 0-M) corresponding to light source 130-1. The predefined setting may indicate a light intensity, color, blink rate, and/or other characteristic of light to be emitted by light source 130-1 during the medical procedure. The predefined setting may minimize an amount of distraction that light source 130-1 may impart to users within medical environment 10 (shown in FIG. 1A).

Furthermore, a location of each of light sources 130 within medical environment 10 (shown in FIG. 1A) may be used to determine which of light sources 130 should be adjusted for use during the medical procedure. Continuing the example above, a setting of light sources 130-2 and 130-4 may not have been adjusted, while a setting of light source 130-3 may have been adjusted. In this example, light source 130-3 may be located proximate to light source 130-1, whereas light sources 130-2 and 130-4 may not be located proximate to light sources 130-1 (and 130-3) within medical environment 10. Thus, in this example, light emitted by light sources 130-2 and 130-4 may not be detectable by optical sensors 132-1 and 132-3 of light sources 130-1 and 130-3, respectively. On the other hand, light emitted by light source 130-3 may be detectable by light source 130-1, at least because of the location of light source 130-1. Therefore, trigger detection subsystem 110 of computing system 102 may determine that light source 130-1 should be adjusted based on a setting of light source 130-3 being adjusted and light source 130-3 being located proximate to light source 130-1.

Trigger detection subsystem 110 may be configured to detect motion within medical environment 10 and, based on the detected motion, may cause one or more of light sources 130 to be adjusted for use during the medical procedure. For example, motion within medical environment 10 of FIG. 1A may be detected using motion sensors. Each of light sources 130 may include a motion sensor configured to detect motion within medical environment 10. Alternatively or additionally, motion sensors may be deployed at various locations within medical environment 10 (e.g., on walls 148, ceiling 150, medical devices 120, etc.). In some examples, the movements of users within medical environment 10 may correspond to certain phases of the medical procedure being performed. Therefore, identifying the movements may indicate when to adjust the setting of one or more of light sources 130 for use during the medical procedure. Additionally or alternatively, room cameras 146 may also be configured to detect motion based on an analysis of objects located within medical environment 10 and the changes of those objects' positions within medical environment 10 over time.

Figure 5A:
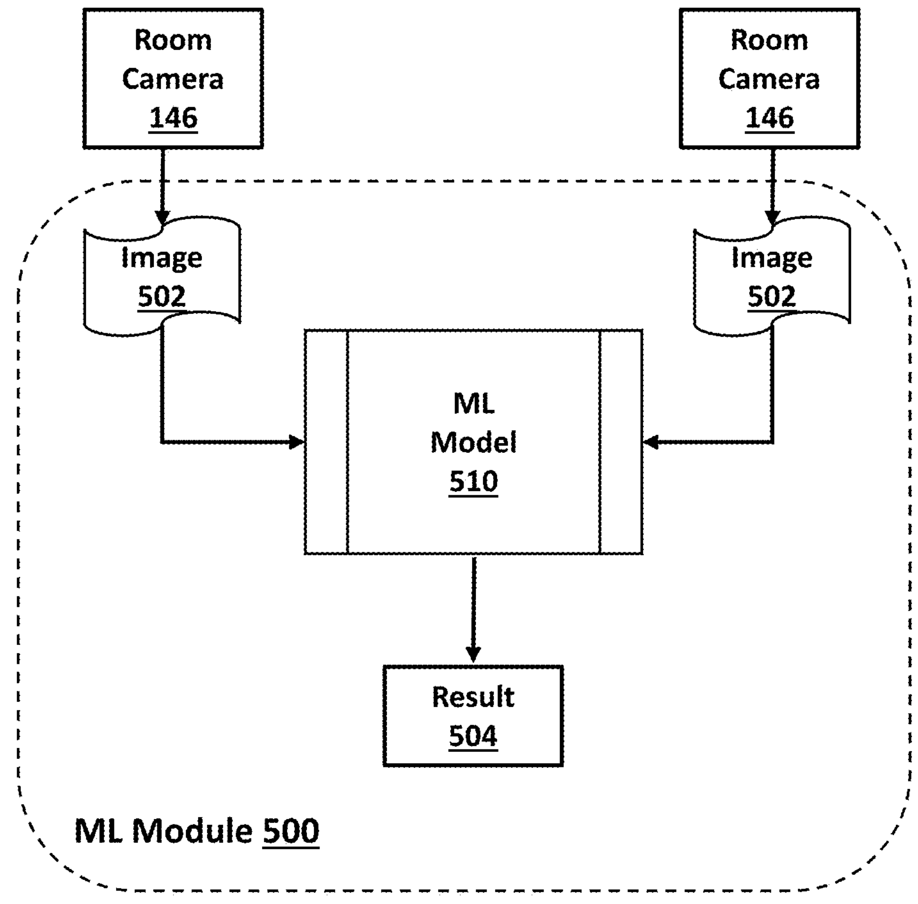
FIGS. 5A-5B illustrate example machine learning modules for implementing a machine learning model to analyze images, according to some aspects.

Trigger detection subsystem 110 may be configured to determine when one or more of light sources 130 are to be adjusted for use during a medical procedure based on one or more objects being recognized within medical environment 10 (shown in FIG. 1A). For example, a first set of room cameras 146 may be configured to capture a first set of images of medical environment 10. A second set of room cameras 146 may capture a second set of images, which may be used together and/or separately to determine whether any objects are present within medical environment 10. Each of the aforementioned room cameras 146 may transmit the captured images of medical environment 10 to one or more machine learning modules in computing system 102. As an example, with reference to FIG. 5A, a machine learning (ML) module 500 may be configured to receive images 502 from room cameras 146. ML module 500 may be implemented by trigger detection subsystem 110. Images 502 may depict the same or different portions of medical environment 10. For example, one of room cameras 146 may capture an image of one side of medical environment 10 while another one of room cameras 146 may capture an image of the other side of medical environment 10. These images may be combined to obtain an image of an entirety of medical environment 10. Alternatively, these images may be processed individually.

Some of room cameras 146 may capture different types of images. For example, one of room cameras 146 may capture high-resolution images, while another one of room cameras 146 may capture infrared images. Additionally, room cameras 146 may capture multiple images at a time. For example, room cameras 146 may capture X images within Y seconds and provide X captured images to computing system 102. Computing system 102 (via trigger detection subsystem 110) may be configured to aggregate the X captured images and analyze the aggregated images to determine whether any objects are present within medical environment 10.

For example, images 502 may be provided to a machine learning (ML) model 510 executable by ML module 500. ML model 510 may be trained to detect certain objects within an image. For example, ML model 510 may be trained to detect objects typically found within medical environment 10 while a medical procedure is being performed. Additionally or alternatively, ML model 510 may be trained to identify phases of the medical procedure (i.e., surgical phases), users, activities performed by users (e.g., surgical activities), anatomical structures, dimensions of those anatomical structures, or other items. Training data used to train ML model 510 may include images depicting various medical objects. ML model 510 may generate predictions of which medical objects, if any, are depicted within the training data images. The predictions may be compared to ground truth information included with the training data. Parameters of ML model 510 (e.g., weights, biases of nodes, etc.) may be adjusted based on the comparisons, and the process may repeat a predefined number of times and/or until ML model 510 outputs predictions at an accuracy greater than or equal to a threshold model accuracy level (e.g., greater than 85% accuracy, greater than 95% accuracy, etc.).

As mentioned above, ML model 510 may receive images 502 from room cameras 146 (as well as other cameras) depicting medical environment 10 (shown in FIG. 1A). ML model 510 may output an object detection result 504. Object detection result 504 may include an indication as to whether one or more objects were detected within images 502. Object detection result 504 may instead or additionally include an indication of the particular objects that were detected (if any). As an example, object detection result 504 may indicate that one or more objects from a predefined set of objects were detected within images 502. Detection of the one or more objects from the predefined set of objects within images 502 may indicate that a medical procedure is being performed within medical environment 10. Accordingly, trigger detection subsystem 110 may generate a notification that a setting of one or more of light sources 130 is to be adjusted for use during the medical procedure. The notification may be provided to light source adjustment subsystem 112, which may output the notification or instructions generated based on the notification (e.g., to light source adjustment subsystem 112) to cause a setting of one or more of light sources 130 to be adjusted for use during the medical procedure.

Optionally, the notification provided by the trigger detection subsystem 110 to the light source adjustment subsystem 112 may include information about which light sources 130 should be adjusted. The trigger detection subsystem 110 may determine which light sources 130 should be adjusted based on detecting the light sources 130 in images 502 from room cameras 146. The ML model 510 may be configured to detect one or more light sources 130 in images 502 and object detection result 504 may include information associated with the detection of the one or more light sources 130 in the images 502. The information may include a type of light source 130 and/or an identity of the light source 130. The identity of the light source 130 may be determined based on a visual identification captured in the images 502, such as a QR code that includes identity information for the light source 130. The trigger detection subsystem 110 may generate a notification for transmitting to the light source adjustment subsystem 112 based on the object detection result 504. The notification may include an identifier for a light source 130 detected in the images 502 and/or may include an indicator of a type of light source 130. Optionally, the trigger detection subsystem 110 may access a database storing identifiers of light sources 130 associated with one or more medical environments 10 and may obtain identifiers for light sources 130 detected in the images 502 for including in the notification. For example, the object detection result 504 may include an indication that a light source of type X was detected, the trigger detection subsystem 110 may query the database for which light sources 130 of type X are associated with medical environment 10 associated with the images 502, and may obtain an identifier for the one or more light sources 130 that are associated with the medical environment 10. The trigger detection subsystem 110 may include the resulting identifier(s) in the notification that it outputs to the light source adjustment subsystem 112. The light source adjustment subsystem 112 may adjust the light sources 130 identified in the notification. For example, with reference to FIG. 4B, the trigger detection subsystem 110 may detect light source 130-1 and light source 130-3 in images 502 but not light source 130-2 or light source 130-4 and may output a notification to light source adjustment subsystem 112 that light sources 130-1 and 130-3 should be adjusted. Light source adjustment subsystem 112 may respond to the notification by adjusting light sources 130-1 and 130-3 but not light source 130-2 and light source 130-4.

In addition to or instead of determining whether images 502 from room cameras 146 and camera 152 disposed on surgical light 154 depict any objects, ML model 510 may be configured to measure an ambient light level of medical environment 10 (shown in FIG. 1A). For example, images 502 may be analyzed to estimate an ambient light level of medical environment 10. As mentioned above, different devices within medical environment 10 may contribute to light pollution (e.g., light sources 130, surgical light 154, overhead light 95, monitor 14, touchscreen 22, etc.). ML model 510 may analyze images 502 to estimate an ambient light level within medical environment 10 and compare the ambient light level to a threshold ambient light level. Result 504 may indicate a result of the comparison. For example, result 504 may indicate that the ambient light level is less than the threshold ambient light level, indicating that one or more of light sources 130 are to be adjusted for use during a medical procedure. Result 504 may instead or additionally include the estimated ambient light level.

In addition to or instead of determining whether images 502 from room cameras 146 depict any objects, ML model 510 may be configured to detect motion within medical environment 10. For example, images 502 may be analyzed to determine whether one or more objects representing a medical device (e.g., endoscope 142) is being used for a medical procedure. Different medical devices 120 may perform different functions, each corresponding to an expected set of motions. For example, a first set of motions may be expected for endoscope 142 when used for endoscopic procedures. ML model 510 may analyze images 502 to determine whether motion has been detected, and if so, whether that motion is indicative of medical device 120 being used for the medical procedure. Thus, object detection result 504 may include an indication of whether a detected object is in motion. For example, in addition to identifying camera head 140 of endoscope 142, ML model 510 may determine that camera head 140 of endoscope 142 is being used for a medical procedure, which may be indicated by object detection result 504. Detecting that one or more of medical devices 120 is being used for a medical procedure may cause one or more of light sources 130 to be adjusted for use during the medical procedure. For example, trigger detection subsystem 110 may receive object detection result 504 indicating that camera head 140 of endoscope 142 is being used for a medical procedure. Based on object detection result 504 indicating that camera head 140 of endoscope 142 is being used for the medical procedure, trigger detection subsystem 110 may generate a notification that a setting of one or more of light sources 130 is to be adjusted for use during the medical procedure. The notification may be provided to light source adjustment subsystem 112, which may output the notification or instructions generated based on the notification (e.g., to light source adjustment subsystem 112) to cause a setting of one or more of light sources 130 to be adjusted for use during the medical procedure.

Figure 5B:
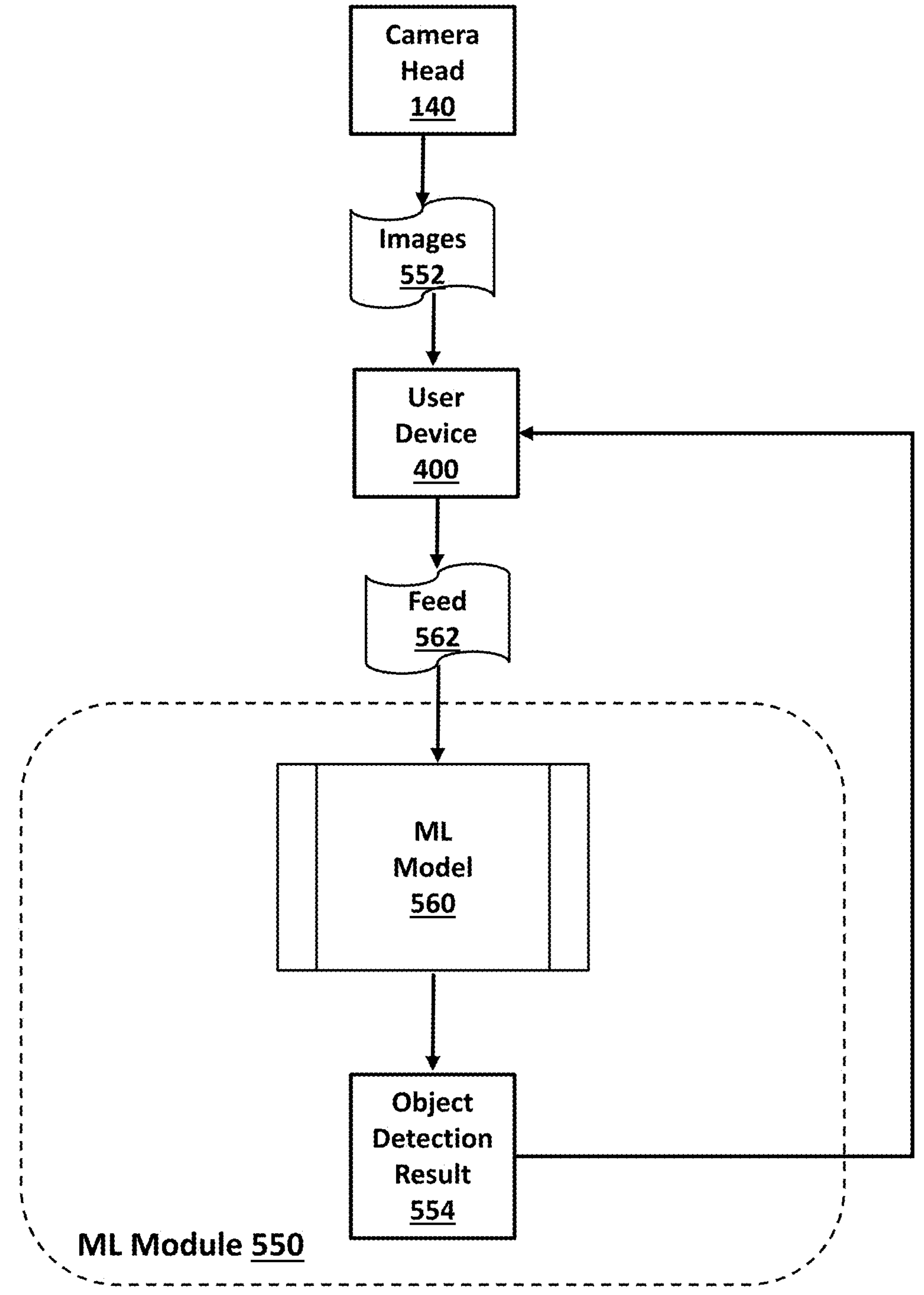

Trigger detection subsystem 110 may be configured to determine when one or more of light sources 130 are to be adjusted for use during a medical procedure based on one or more objects being recognized within a surgical video feed or other images captured via medical device 120. For example, camera head 140 of endoscope 142 may be configured to capture images of patient 12 (e.g., internal cavities of patient 12). As an example, with reference to FIG. 5B, a machine learning (ML) module 550 may be configured to receive one or more images 552 from camera head 140. Images 552 may depict internal anatomical structures or other medical objects viewable during different aspects of a medical procedure. For example, images 552 may depict particular anatomical structures (e.g., gallbladder, liver, etc.).

Images 552 may be provided to user device 400 (shown in FIG. 4A), which may be configured to display a surgical video feed 562 via display 402. Images from surgical video feed 562 may instead or additionally be provided as input to a machine learning (ML) model 560. ML model 560 may be executed locally on user device 400 and/or camera head 140, via computing system 102, by another computing system, and/or a combination thereof. ML model 560 may be trained to detect certain objects within an image. For example, ML model 560 may be trained to detect objects typically seen as a medical procedure is being performed. ML model 560 may instead or additionally be trained to identify phases of the medical procedure (i.e., surgical phases), anatomical structures, dimensions of those anatomical structures, or other items. Training data used to train ML model 560 may include images depicting various medical objects. ML model 560 may generate predictions of which medical objects, if any, are depicted within those images. The predictions may be compared to ground truth information included with the training data. Parameters of ML model 560 (e.g., weights, biases of nodes, etc.) may be adjusted based on the comparisons, and the process may be repeated a predefined number of times and/or until ML model 560 outputs predictions at an accuracy greater than or equal to a threshold model accuracy level (e.g., greater than 85% accuracy, greater than 95% accuracy, etc.).

As mentioned above, ML model 560 may receive images from surgical video feed 562. Based on the received images, ML model 560 may output object detection result 554. Object detection result 554 may include an indication as to whether any objects were depicted in surgical video feed 562. Object detection result 554 may instead or additionally include an indication of which objects were detected. As an example, object detection result 554 may indicate that one or more objects of a predefined set of objects were depicted within frames of surgical video feed 562. The one or more objects from the predefined set of objects may be associated with a particular phase of a medical procedure. Therefore, object detection result 554 may indicate that (i) a medical procedure is being performed within medical environment 10 (shown in FIG. 1A) and/or (ii) a particular phase of the medical procedure is being performed. Accordingly, trigger detection subsystem 110 may generate and output a notification to cause a setting of one or of more light sources 130 to be adjusted for use during the medical procedure. The notification may instead or additionally cause a setting of display 402 of user device 400 (shown in FIG. 4A) to be adjusted. This may include increasing and/or decreasing a contrast, brightness, clarity, or other characteristic of display 402. For example, a brightness of display 402 may be adjusted to a predefined brightness level. The predefined brightness level may refer to a brightness for display 402 that improves viewability of the content rendered on display 402. User device 400, computing system 102, or another device may be configured to send an instruction to display 402 to cause a brightness of display 402 to be adjusted to the predefined brightness level. Object detection result 554 may be provided to user device 400, which may be configured to display object detection result 554 via display 402. Object detection result 554 may be presented with surgical video feed 562. For example, object detection result 554 may comprise a marker (e.g., a bounding box) enclosing the detected object(s). The marker may be displayed via display 402 as an overlay to surgical video feed 562 (not illustrated).

Returning to FIG. 1B, trigger detection subsystem 110 may access scheduling data stored in scheduling data database 168. The scheduling data may include indications of when medical environment 10 (shown in FIG. 1A) is being used, what medical procedure is being performed within medical environment 10, who is performing the medical procedure (e.g., surgeons, medical staff, etc.), or other information. The scheduling data may be used to determine a start time of a medical procedure and thus a time at which light sources 130 are to be adjusted (e.g., based on the medical procedure and the start time). For example, the scheduling data may indicate that a particular surgery is being performed at time T. Based on the particular surgery being performed, trigger detection subsystem 110 may determine that X minutes after the surgery begins, one or more of light sources 130 are to be adjusted to a predefined setting. Scheduling data may indicate which of light sources 130 are to be adjusted. For example, the scheduling data may indicate that 10 minutes after the surgery begins, one of light sources 130 is to be adjusted to a predefined setting associated with use of that light source 130 during the surgery. Trigger detection subsystem 110 may determine a light source identifier associated with the one of light sources 130 that is to be adjusted. For example, trigger detection subsystem 110 may determine that the identified light source 130 has a light source ID of "Source_ID_0." Trigger detection subsystem 110 may access data structure 200 of settings database 162 (as seen in FIG. 2), and may retrieve one of the light settings (e.g., setting_00-setting_M0) associated with light source ID "Source_ID_0." The retrieved light setting (e.g., setting_00) may be used, for example, by light source adjustment subsystem 112 of FIG. 1B, to cause a setting of the identified light source 130 to be adjusted.

Figure 6:
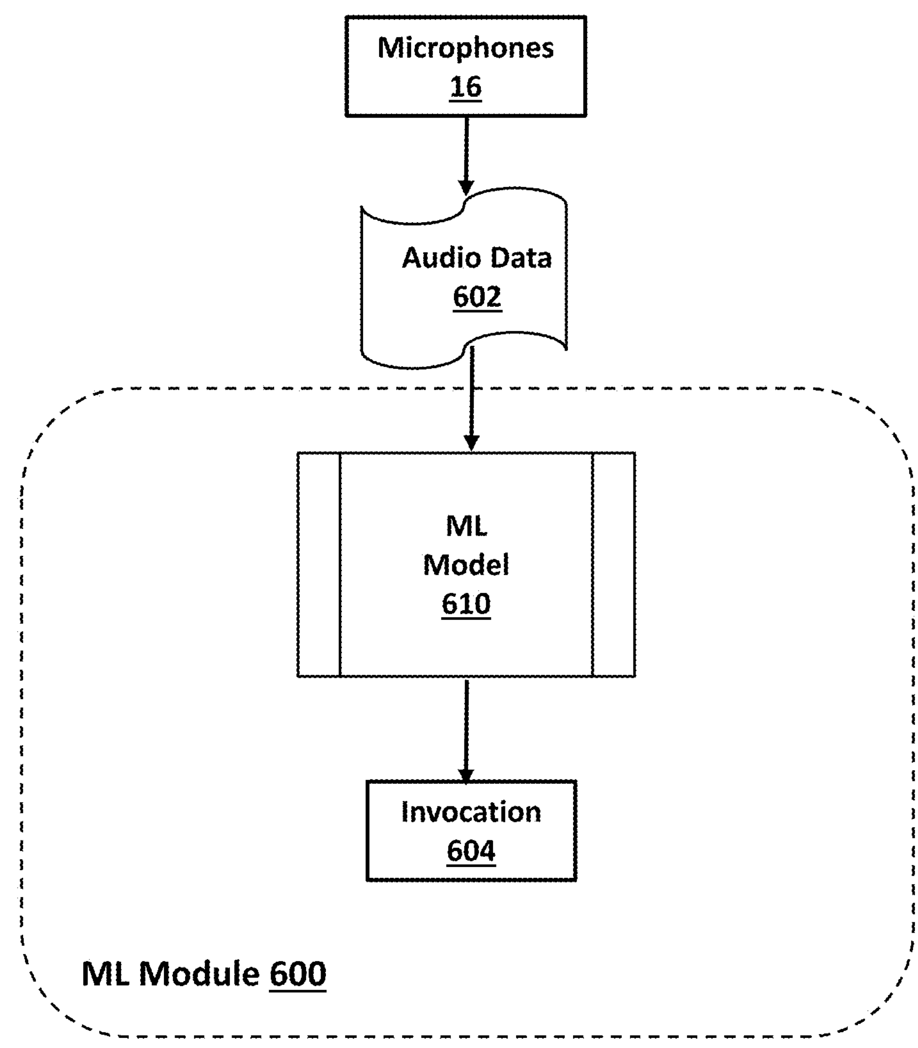
FIG. 6 illustrates an example machine learning model for implementing a machine learning model to analyze voice commands, according to some aspects.

Trigger detection subsystem 110 may be configured to detect voice commands to cause one or more of light sources 130 within medical environment 10 to be adjusted for use during a medical procedure. As an example, with reference to FIG. 6, machine learning (ML) module 600 may be implemented by trigger detection subsystem 110 to detect voice commands. ML module 600 may be configured to receive audio data 602 representing audio signals captured by microphones 16 within medical environment 10 (shown in FIG. 1A). Microphones 16 may be integrated into and/or coupled to medical devices 120, light sources 130, other user devices within medical environment 10, one or more far field microphones, and/or other audio sensors. Microphones 16 may be configured to continually capture audio signals. Microphones 16 may be configured to output audio data 602 representing the captured audio signals. Audio data 602 may be provided to ML module 600 for analysis. Microphones 16 may instead or additionally be configured to capture audio signals in response to an input (e.g., a user pressing a button) and/or detection that a keyword and/or phrase has been uttered. For example, after uttering a particular keyword, microphones 16 may begin capturing audio signals and sending audio data 602 representing those audio signals to ML model 610.

ML model 610 may include one or more machine learning models trained to perform various speech processing tasks. For example, ML model 610 may include models trained to convert audio data 602 into text, identify parts-of-speech within the text, identify named entities based on the identified parts-of-speech, use natural language understanding (NLU) to determine an intent of the voice command, and/or perform other tasks (not illustrated in FIG. 6 for simplicity). ML model 610 may output invocation 604, which may indicate that a setting of one or more of light sources 130 (shown in FIGS. 1A-1B) is to be adjusted to a predefined setting. Invocation 604 may specify which of light sources 130 are to be adjusted, as well as the predefined setting those light sources are to be adjusted to. For example, if the utterance is "Set Encoder/Decoder light to Dark Mode," then ML model 610 may indicate that a setting of a light source 130 (e.g., an LED located on one or more of encoder/decoder devices 700) within medical environment 10 is to be adjusted to a predefined setting associated with the medical procedure.

Trigger detection subsystem 110 may be configured to determine when a setting of one or more of light sources 130 are to be adjusted to a default setting. The default setting may be associated with an end of the medical procedure. For example, when the medical procedure has ended, or is approaching its end, one or more of light sources 130 may be adjusted to emit light that differs from the light emitted during the medical procedure. For example, one of light sources 130 may emit light having a first intensity during medical procedures (e.g., 20% of maximum luminosity) whereas during non-medical procedure times, that light source 130 may emit light at a second intensity higher than the first intensity (e.g., 90% of maximum luminosity). Trigger detection subsystem 110 may be configured to use any of the aforementioned systems and methods to determine when the medical procedure has completed to cause a setting of one or more of light sources 130 to be adjusted to the default setting. The default setting may be stored in settings database 162. For example, with reference to FIG. 2, one or more of light settings 0-M may represent a default setting for a corresponding light source 130.

Returning to FIG. 1B, trigger detection subsystem 110 may be configured to cause one or more of light sources 130 to be disabled. The disablement of the one or more light sources 130 may reduce light pollution in medical environment 10 by removing the one or more light sources' light contribution.

Light source adjustment subsystem 112 may be configured to cause one or more of light sources 130 to adjust their respective settings from a current setting to a predefined setting associated with the medical procedure. Light source adjustment subsystem 112 may receive a notification from trigger detection subsystem 110, which may indicate that a trigger has been detected. The trigger, as mentioned above, may indicate that a setting of one or more of light sources 130 are to be adjusted for use during the medical procedure. The notification may include an indication of which of light sources 130 are to be adjusted. Optionally, the notification may instead or additionally include a current setting of one or more of light sources 130, the predefined setting those light sources 130 are to be adjusted to, or other information.

Light source adjustment subsystem 112 may be configured to retrieve a setting for one or more of light sources 130 based on the notification received from trigger detection subsystem 110. For example, light source adjustment subsystem 112 may access data structure 200 of settings database 162 (shown in FIG. 2) and retrieve one or more predefined settings for that light source (e.g., one or more of light settings 0-M). The retrieved setting may be used by light source adjustment subsystem 112 to cause the one or more light sources 130 to adjust one or more aspects of their respective light profiles. For example, the predefined setting may indicate a color, intensity, blink rate, and/or other aspect of light to be emitted by one of light sources 130. By adjusting one or more of the aforementioned light characteristics, light pollution within medical environment 10 may be reduced while the medical procedure is being performed.

Light source adjustment subsystem 112 may be configured to cause other devices or components of medical environment 10 to adjust their respective settings. For example, based on the notification being received indicating that one or more of light sources 130 are to be adjusted to a predefined setting (as described above), light source adjustment subsystem 112 may determine that a setting of a display device (e.g., display 402 of user device 400 shown in FIG. 4A, additional monitor 14, touchscreen monitor 22, etc.), medical device 120, surgical light 154, or another device within medical environment 10 is to be adjusted. As an example, light source adjustment subsystem 112 may cause a setting of an LED located on one or more of encoder/decoder devices 700 (e.g., used for transmission of audio/video data from camera head 140 of endoscope 142 to monitor 14 and/or touchscreen 22) to be adjusted for use during the medical procedure. This adjustment may include increasing or decreasing an intensity of light emitted by the LED (e.g., one of light sources 130), increasing or decreasing a blink rate of the light emitted by the LED, changing a color of the light emitted by the LED, or adjusting another aspect of the LED on encoder/decoder devices 700. As another example, with reference to FIG. 4A, light source adjustment subsystem 112 may cause a setting for display 402 of user device 400 to be adjusted for use during the medical procedure. This adjustment may include increasing or decreasing a brightness of display 402, increasing or decreasing a contrast of display 402, or adjusting another aspect of display 402. As another example, light source adjustment subsystem 112 may cause a setting for surgical light 154 to be adjusted for use during the medical procedure. This adjustment may include adjusting an intensity of light emitted by surgical light 154, adjusting a color (or hue) of the light emitted by surgical light 154, or adjusting another aspect of surgical light 154.

Light source adjustment subsystem 112 may be configured to adjust a setting of one or more of light sources 130 to a default setting associated with the medical procedure being over or otherwise no longer being performed. For example, light source adjustment subsystem 112 may cause a setting of one or more of light sources 130 to be adjusted from the predefined setting (associated with the medical procedure) to the default setting. In the default setting, one or more of light sources 130 may have a different color, intensity, and/or blink rate as compared to the color, intensity, and/or blink rate of the one or more of light sources 130 corresponding to the predefined setting.

Light source adjustment subsystem 112 may be configured to disable one or more of light sources 130 such that those light sources 130 no longer emit light. For example, in response to the setting of one of light sources 130 being adjusted, light source adjustment subsystem 112 may disable another one of light sources 130, surgical light 154, monitor 14, touchscreen 22, or other devices within medical environment 10 of FIG. 1A.

Light source adjustment subsystem 112 may be configured to update the predefined setting of one or more of light sources 130. For example, after one or more of light sources 130 has been adjusted to the predefined setting, an instruction may be received to adjust those light sources 130 to a new setting. The new setting may indicate a different intensity, color, hue, blink rate, etc., of light emitted by those light sources 130. The instruction may be received by light source adjustment subsystem 112 from one or more devices in medical environment 10 (shown in FIG. 1A). For example, the instruction may be input by a user (e.g., a surgeon, medical staff, etc.) via touchscreen 22. As another example, the user may utter a voice command that is detected by microphones 16 of medical environment 10. Microphones 16 may output audio data representing the voice command to computing system 102, which may generate the instructions based on a determined intent of the voice command. Light source adjustment subsystem 112 may provide the new setting to settings database 162, which may store the new setting in data structure 200 (shown in FIG. 2) in association with the one or more of light sources 130 that had their settings adjusted.

Figure 7:
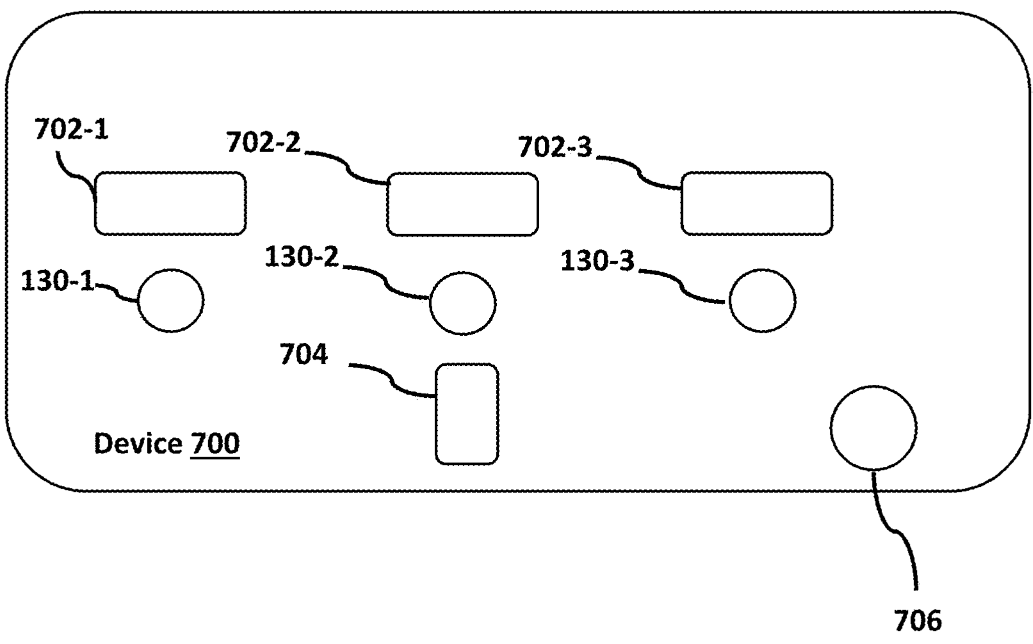
FIG. 7 illustrates an example device including one or more light sources, according to some aspects.

As mentioned previously, medical environment 10 of FIG. 1A may include a vast amount of light sources 130. FIG. 7 illustrates an example encoder/decoder device 700 that includes one or more light sources, according to some aspects. Encoder/decoder device 700 may be located within medical environment 10 (shown in FIG. 1A) and may include one or more light sources 130. Light sources 130 may be integrated within encoder/decoder device 700. Alternatively or additionally, one or more other light sources 130 may be coupled to encoder/decoder device 700. As an example, encoder/decoder device 700 may be coupled to medical device 120 (e.g., endoscope 142). Encoder/decoder device 700 may be used for transmitting audio/video from a camera (e.g., camera head 140 of endoscope 142) to a display device (e.g., monitor 14, touchscreen 22, etc.), surgical table 17, a display device (e.g., monitor 14, touchscreen 22, etc.), computing system 102, and/or other devices. Encoder/decoder device 700 may instead or additionally be a component of another device. For example, encoder/decoder device 700 may represent an interface communicably coupled to medical device 120. The interface may be used to control certain functionalities of medical device 120. Encoder/decoder device 700 may include one or more processors, memory, storage, communications components, or other components, such as those described below with respect to computing system 900 of FIG. 9.

As shown in FIG. 7, encoder/decoder device 700 may include one or more light sources, such as light sources 130-1, 130-2, and 130-3 (collectively referred to herein as "light sources 130"). Although three light sources 130 are depicted, persons of ordinary skill in the art will recognize that the quantity, size, shape, arrangement, or other aspects of light sources 130 may differ from that depicted in FIG. 7, and the foregoing should not be construed as being limiting. Light sources 130 of encoder/decoder device 700 may be configured to emit light based on a light profile. This light profile may specify a particular color, intensity, blink rate, or other characteristics of the light to be emitted by light sources 130. For example, the light profile may be used by light source adjustment subsystem 112 (shown in FIG. 1B) to cause one or more of light sources 130 to emit light at a constant intensity and/or color. Alternatively or additionally, the light profile may be used by light source adjustment subsystem 112 to cause one or more of light sources 130 to emit light at a constant intensity, but with varying colors. The color of the light emitted by light sources 130 may vary at a particular frequency, which may be pre-programmed (e.g., a first color light is emitted, followed by a second color light being emitted, followed by a third color light being emitted, etc., where each color is emitted for a same amount of time or different amounts of time). The light profile may indicate that light having a same color but a varying intensity is to be emitted by one or more of light sources 130. For example, the light emitted by light sources 130 may be gradually and/or rapidly brightened and subsequently dimmed (or vice versa). The light profile may indicate that light emitted by light sources 130 may have a constant color but may be programmed to change intensity at a particular frequency. For example, the light emitted by one or more of light sources 130 may be gradually increased over a first duration, and then dimmed gradually over a second duration. The change in light intensity may also be referred to as a blink rate, where the intensity switches between a first intensity level and at least a second intensity level at a particular frequency. Different light profiles (e.g., different blink rates, light intensities, colors, etc.) may be associated with different functionalities of encoder/decoder device 700. For example, a first blink rate may be associated with a first functionality of encoder/decoder device 700, while a second blink rate may be associated with a second functionality of encoder/decoder device 700.

Light sources 130 may be associated with different components of encoder/decoder device 700. For example, light source 130-1 may correspond to interface 702-1, light source 130-2 may correspond to interface 702-2, and light source 130-3 may correspond to interface 702-3. Interfaces 702-1, 702-2, and 702-3 (collectively "interfaces 702") may be associated with different functionalities of encoder/decoder device 700. For example, interface 702-1 may communicably couple encoder/decoder device 700 with medical device 120, while interface 702-2 may communicably couple encoder/decoder device 700 with additional monitor 14. In this example, light sources 130-1 and 130-2 may be programmed to emit light based on a light profile associated with the functionalities of encoder/decoder device 700 facilitated by interfaces 702-1 and 702-2, respectively.

At different times during the medical procedure, different functionalities of encoder/decoder device 700, or other devices similar to encoder/decoder device 700, may be used. For example, during a first phase of the medical procedure, a first functionality of encoder/decoder device 700 may be used, whereas during a second phase of the medical procedure, a second functionality of encoder/decoder device 700 may be used. The different functionalities may be associated with different interfaces 702. Therefore, at different times during the medical procedure, one or more of light sources 130 may emit light, while at other times during the medical procedure, the one or more light sources 130 may emit different light (e.g., light having a different intensity, color, blink rate, etc.), or may not emit light.

Some of light sources 130 may be controlled via a mechanical input mechanism 704 of encoder/decoder device 700. For example, input mechanism 704 may be used to control certain aspects of light emitted by one or more of light sources 130. For example, input mechanism 704 may change the state of light source 130-2 (e.g., turn the light source on and/or off), increase or decrease an intensity of light emitted by light source 130-2, and/or change a blink rate of light source 130-2 (e.g., change from blinking at a particular frequency, to constant (or otherwise not blinking), to disabled). Input mechanism 704 may be implemented as a physical input mechanism, such as a switch, a toggle, a physical button, or another type of input mechanism. Additionally or alternatively, input mechanism 704 may be implemented using a graphical user interface (GUI) rendered on a display device (e.g., on a display of encoder/decoder device 700, monitor 14 and/or touchscreen 22 illustrated in FIG. 1A, etc.).

Input mechanism 704 may be used to place one or more light sources 130 in a mode for use during a medical procedure (e.g., medical procedure mode). In this mode, light sources 130 may be programmed to emit light having a particular light profile. The light profile may indicate characteristics that the emitted light should have during the medical procedure. For example, the light profile may indicate a color, intensity, blink rate, another characteristic, and/or a combination thereof.

Although input mechanism 704 is depicted as being part of encoder/decoder device 700, it may additionally or alternatively be placed on another device within medical environment 10. For example, a controller, computing system, or other device may include an input mechanism that is the same or similar to input mechanism 704. Invocation of this input mechanism may cause a setting of one or more of light sources 130 to be adjusted in a same or similar manner as described above.

Encoder/decoder device 700 may include a sensor 706. As an example, sensor 706 may be an optical sensor configured to measure an ambient light level of medical environment 10 (shown in FIG. 1A). In this example, sensor 706 may be the same or similar to optical sensor 132 shown in FIG. 1A. As another example, sensor 706 may be an audio sensor, a motion sensor, an image sensor (e.g., cameras), other sensors, and/or combinations thereof. Although a single instance of sensor 706 is depicted, encoder/decoder device 700 may include additional instances of sensor 706 and/or different types of sensors. Furthermore, sensor 706 may be included within other devices or as one or more stand-alone devices within medical environment 10.

As mentioned above, light sources 130 of encoder/decoder device 700 may cause light pollution within medical environment 10 (shown in FIG. 1A). This light pollution can impact the clarity of images displayed on monitor 14 and/or touchscreen 22 in medical environment 10, which can hinder the performance of a medical procedure. Additionally, a light profile of the light emitted by light sources 130 may distract or bother users within medical environment 10 (e.g., surgeons, medical staff, etc.), which can further hinder the performance of the medical procedure.

Figure 8:
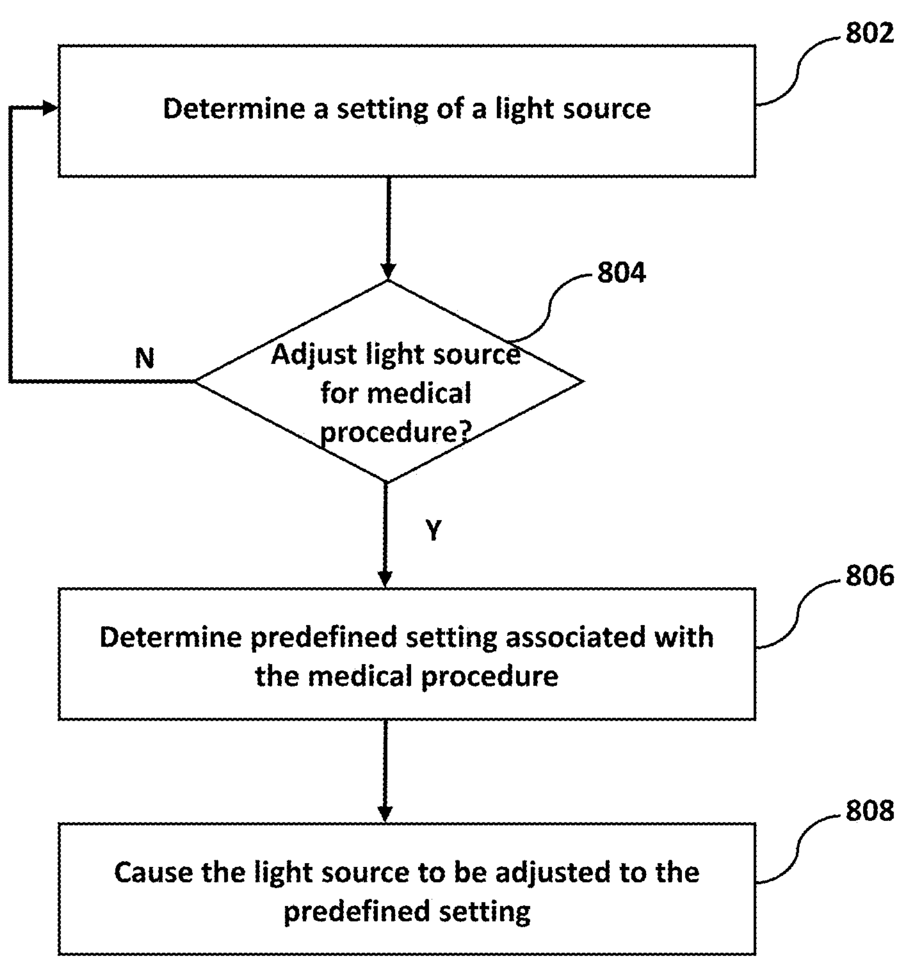
FIG. 8 illustrates a flowchart of an example process for reducing light pollution within a medical environment, according to some aspects.

FIG. 8 illustrates a flowchart of an example process 800 for reducing light pollution within a medical environment, according to some aspects. Process 800 may begin at step 802 where a setting of a light source may be determined. For example, the light source may refer to one or more of light sources 130 located within medical environment 10. Determining the setting of light sources 130 may include continually monitoring light sources 130. This may include determining a current setting of some or all of light sources 130 at a particular cadence (e.g., every second, every 30 seconds, every minute, etc.). Optionally, the settings of some or all of light sources 130 may be tracked and stored in memory to identify changes in the settings over a certain time period (e.g., over a day, over a week, etc.). Step 802 may be performed by a subsystem that is the same or similar to trigger detection subsystem 110.

At step 804, a determination may be made as to whether the light source (e.g., the light source from step 802) is to be adjusted for use during the medical procedure. Adjusting one or more of light sources 130 for use during the medical procedure may reduce and/or minimize light pollution within medical environment 10 (shown in FIG. 1A). Light sources 130 may be adjusted to a predefined setting that reduces and/or minimizes light pollution within medical environment 10. For example, the predefined setting may indicate a color, intensity, blink rate, or other aspect of light to be emitted by one or more of light sources 130.

The determination of whether a light source is to be adjusted for use during the medical procedure may be based on a variety of factors. For example, the determination may be made based on receipt of a notification to adjust a setting of one or more of light sources 130 for use during the medical procedure. As another example, the determination may be made based on a detected ambient light level of medical environment 10 (shown in FIG. 1A) being less than or equal to a predefined ambient light threshold associated with the medical procedure being performed. The ambient light level may be determined based on a measurement of optical sensors 132 (shown in FIGS. 1A and 4B) of medical environment 10. The ambient light level may instead or additionally be determined using one or more machine learning models trained to estimate an ambient light level of medical environment 10 using images captured by room cameras 146. As another example, the determination may be made based on objects or activities detected within medical environment 10 (e.g., particular anatomical structures being detected, surgical activities of the medical procedure being detected, etc.). As another example, the determination may be made based on a voice command detected by one or more audio sensors located within medical environment 10. As another example, the determination may be based on a user input being detected (e.g., a user pressing a button). Step 804 may be performed by a subsystem that is the same or similar to trigger detection subsystem 110.

If, at step 804, it is determined that a setting of light sources 130 should not be adjusted, then process 800 may return to step 802. At step 802, the system may continue to monitor light sources 130 to determine whether any light sources 130 have been adjusted for use during a medical procedure. However, if at step 804 it is determined that a setting of light sources 130 should be adjusted, process 800 may proceed to step 806.

At step 806, a predefined setting associated with the medical procedure may be determined. Different medical procedures may benefit from different lighting conditions within medical environment 10. For example, light sources 130 may emit light having different characteristics depending on the medical procedure being performed. For example, one medical procedure may include one of light sources 130 emitting white light at a 70% of maximum luminosity, while another medical procedure may include that same light source 130 emitting green light at 20% of maximum luminosity. Determining which predefined setting to retrieve from settings database 162 may be based on which of light sources 130 are to have their corresponding setting adjusted. The predefined setting may instead or additionally be based on the medical procedure to be performed, preferences of the users (e.g., a surgeon's preferences, medical staff's preferences, etc.), or other factors. For example, one of light sources 130 may emit white light at 70% of maximum luminosity for one surgeon performing a medical procedure, while that same light source 130 may emit light at 50% of maximum luminosity for another surgeon performing the same medical procedure. The predefined setting may be determined based on other aspects of medical environment 10. For example, the predefined setting may be determined based on an ambient light level of medical environment 10. If the ambient light level is equal to or less than a threshold ambient light level, it may be determined that a first predefined setting for light source 130 is to be retrieved from settings database 162. However, if the ambient light level is greater than the threshold ambient light level, then a second predefined setting for light source 130 may be retrieved from settings database 162. Step 806 may be performed by a subsystem that is the same or similar to trigger detection subsystem 110, light source adjustment subsystem 112, and/or by a subsystem that is capable of performing some or all of the functionalities of trigger detection subsystem 110 and light source adjustment subsystem 112.

At step 808, the light source may be adjusted (or caused to be adjusted) to the predefined setting. For example, instructions to adjust a light profile of light emitted by one or more of light sources 130 may be sent to the one or more of light sources 130. As another example, with reference to FIG. 4B, one or more controllers 452 for light sources 130 may receive the instructions to adjust the setting of light emitted by the one or more of light sources 130. The instructions may be generated based on the retrieved predefined setting (e.g., retrieved by computing system 102 of FIG. 1B). For example, the instructions may be generated based on predefined settings stored in data structure 200 of settings database 162, shown in FIG. 2. Step 806 may be performed by a subsystem that is the same or similar to light source adjustment subsystem 112.

Figure 9:
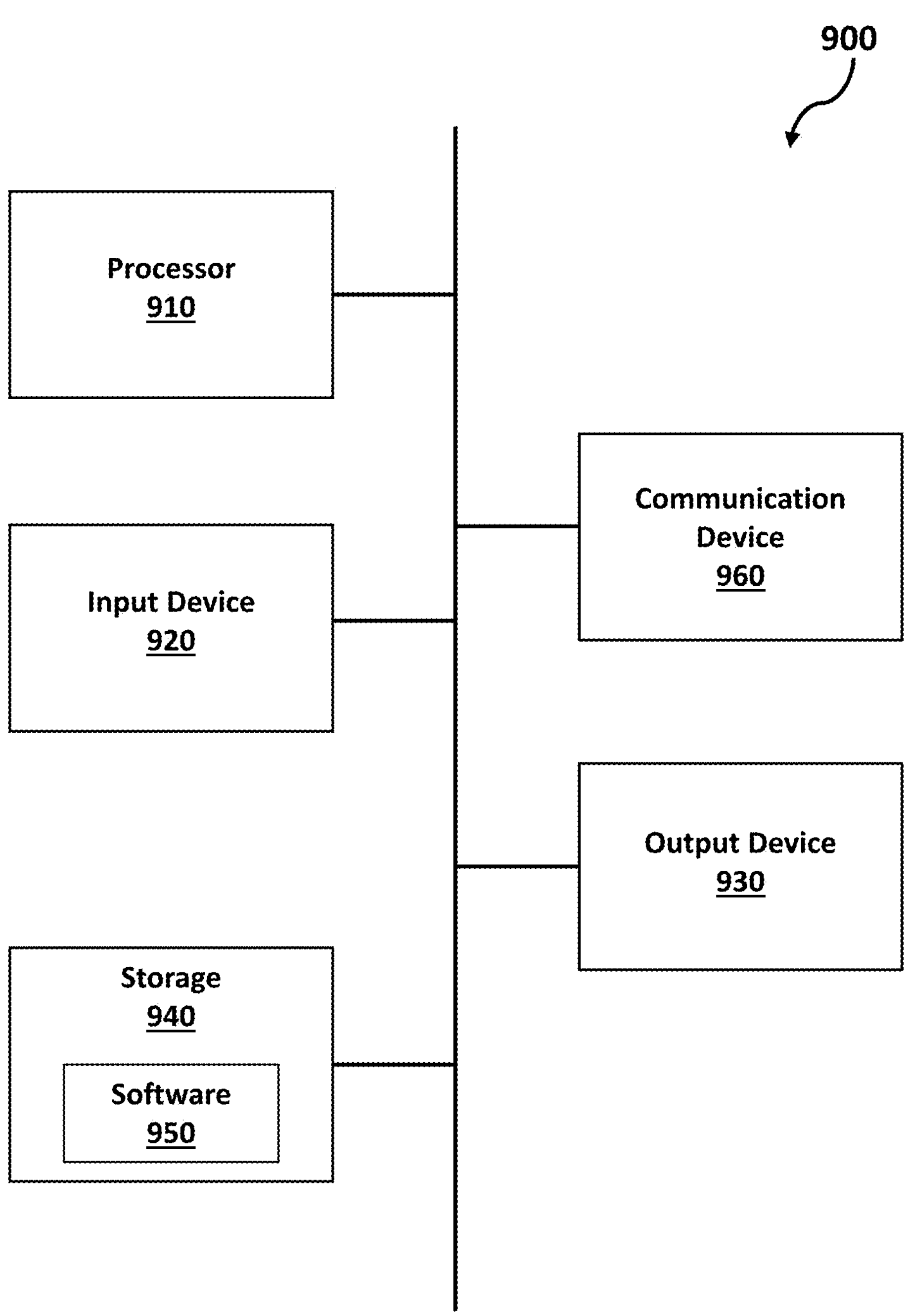
FIG. 9 illustrates an example computing system used for performing any of the techniques described herein, according to some aspects.

FIG. 9 illustrates an example computing system 900, according to some aspects. Computing system 900 may be used for performing any of the processes described herein, including process 800 of FIG. 8, and can be used for any of the systems described herein, including computing system 102 (and the subsystems included therein), medical device 120, light source 130, or other systems/devices described herein. Computing system 900 can be a computer coupled to a network, which can be, for example, an operating room network or a hospital network. Computing system 900 can be a client computer or a server. As shown in FIG. 9, computing system 900 can be any suitable type of controller (including a microcontroller) or processor (including a microprocessor) based system, such as an embedded control system, personal computer, workstation, server, or handheld computing device (portable electronic device) such as a phone or tablet. The system can include, for example, one or more of processor 910, input device 920, output device 930, storage 940, or communication device 960.

Input device 920 can be any suitable device that provides input, such as a touch screen, keyboard or keypad, mouse, gesture recognition component of a virtual/augmented reality system, or voice-recognition device. Output device 930 can be or include any suitable device that provides output, such as a touch screen, haptics device, virtual/augmented reality display, or speaker.

Storage 940 can be any suitable device that provides storage, such as an electrical, magnetic, or optical memory including a RAM, cache, hard drive, removable storage disk, or other non-transitory computer readable medium. Communication device 960 can include any suitable device capable of transmitting and receiving signals over a network, such as a network interface chip or device. The components of the computer can be coupled in any suitable manner, such as via a physical bus or wirelessly.

Software 950, which can be stored in storage 940 and executed by processor 910, can include, for example, the programming that embodies the functionality of the present disclosure (e.g., as embodied in the devices as described above). For example, software 950 can include one or more programs for performing one or more of the steps of the methods disclosed herein.

Software 950 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 940, that can contain or store programming for use by or in connection with an instruction execution system, apparatus, or device.

Software 950 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic, or infrared wired or wireless propagation medium.

Computing system 900 may be coupled to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computing system 900 can implement any operating system suitable for operating on the network. Software 950 can be written in any suitable programming language, such as C, C++, C#, Java, or Python. In various examples, application software embodying the functionality of the present disclosure can be deployed in different configurations, such as in a client/server arrangement or through a Web browser as a Web-based application or Web service, for example.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y," "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively.

The foregoing description, for the purpose of explanation, has been described with reference to specific aspects. However, the illustrative discussions above are not intended to be exhaustive or to limit the invention to the precise forms disclosed. Many modifications and variations are possible in view of the above teachings. The aspects were chosen and described in order to best explain the principles of the techniques and their practical applications. Others skilled in the art are thereby enabled to best utilize the techniques and various aspects with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A computer-implemented method for reducing light pollution in a medical environment, comprising:

determining, by a computing system of the medical environment, that lighting in the medical environment is to be adjusted for use during a medical procedure, the lighting in the medical environment comprising light emitted by a medical light for illumination of a subject for observation during the medical procedure;

identifying, by the computing system, a device in the medical environment that is communicatively connected to the computing system, the device including an indicator light source associated with the light pollution, the indicator light source configured to indicate a functionality of the device;

determining that a setting of the indicator light source associated with the light pollution is to be adjusted to a predefined setting associated with reducing the light pollution during the medical procedure; and causing the setting of the indicator light source associated with the light pollution to be adjusted to the predefined setting.

2. The method of claim 1, wherein determining that the lighting in the medical environment is to be adjusted comprises:

receiving, by the computing system of the medical environment, a selection to use the medical environment for the medical procedure; and sending, by the computing system, a notification to the device, the notification indicating that the setting of the indicator light source associated with the light pollution is to be adjusted.

3. The method of claim 1, wherein determining that the lighting in the medical environment is to be adjusted comprises:

identifying that a setting of the medical light has been adjusted for use during the medical procedure.

4. The method of claim 1, wherein determining that the lighting in the medical environment is to be adjusted comprises:

determining, using one or more optical sensors of the medical environment, that an ambient light of the medical environment has been adjusted for use during the medical procedure, the setting of the indicator light source associated with the light pollution being adjusted based at least in part on the ambient light.

5. The method of claim 1, wherein determining that the lighting in the medical environment is to be adjusted comprises:

receiving, from an image sensor of the medical environment, one or more images depicting the medical environment; and detecting, using a machine learning model, at least one medical object associated with the medical procedure within the one or more images, the setting of the indicator light source associated with the light pollution being adjusted based at least in part on the at least one medical object being detected.

6. The method of claim 1, wherein determining that the lighting in the medical environment is to be adjusted comprises:

receiving, from an image sensor of the medical environment, one or more images depicting the medical environment; and identifying, using one or more machine learning models, an activity of a user within the medical environment based on the one or more images, the setting of the indicator light source associated with the light pollution being adjusted based at least in part on the activity of the user.

7. The method of claim 1, wherein determining that the lighting in the medical environment is to be adjusted comprises:

receiving, using one or more image sensors, one or more images depicting the medical environment; and determining an ambient light level of the medical environment based on the one or more images, the setting of the indicator light source associated with the light pollution being adjusted based at least in part on the ambient light level.

8. The method of claim 1, wherein determining that the lighting in the medical environment is to be adjusted comprises:

detecting, using one or more audio sensors, a voice command to adjust the setting of the indicator light source associated with the light pollution.

9. The method of claim 1, wherein the device comprises a display screen within the medical environment, and causing the setting of the indicator light source associated with the light pollution to be adjusted comprises:

sending an instruction to the display screen within the medical environment, the instruction indicating that a brightness of the display screen is to be reduced to a predefined brightness level.

10. The method of claim 1, wherein determining that the lighting in the medical environment is to be adjusted comprises:

detecting, using one or more optical sensors, the light emitted by the medical light, the emitted light being associated with a light profile; and determining the light profile of the light, the setting of the indicator light source associated with the light pollution being adjusted based at least in part on the light profile.

11. The method of claim 1, wherein determining that the lighting in the medical environment is to be adjusted comprises:

detecting, using one or more optical sensors, light emitted by one or more additional light sources within the medical environment; and determining that a setting of the light emitted by the one or more additional light sources has been adjusted to be the predefined setting.

12. The method of claim 1, further comprising:

receiving an instruction to adjust the indicator light source associated with the light pollution to a new setting differing from the predefined setting; and updating the predefined setting to be the new setting.

13. The method of claim 1, wherein determining that the lighting in the medical environment is to be adjusted comprises:

designating an optical sensor within the medical environment for use in detecting an ambient light level of the medical environment; and determining, using the optical sensor, the ambient light level of the medical environment, the setting of the indicator light source associated with the light pollution being adjusted based at least in part on the ambient light level.

14. The method of claim 1, further comprising:

determining an ambient light level of the medical environment subsequent to the indicator light source associated with the light pollution being adjusted to the predefined setting; and causing light emitted by the medical light to be adjusted for use during the medical procedure based on the ambient light level.

15. The method of claim 1, further comprising:

detecting an ambient light level of the medical environment subsequent to the indicator light source associated with the light pollution being adjusted to the predefined setting;

determining, based on the ambient light level, that the medical procedure has completed; and causing the setting of the at least one indicator light source associated with the light pollution to be adjusted to a default setting corresponding to completion of the medical procedure.

16. The method of claim 1, wherein the predefined setting associated with reducing the light pollution during the medical procedure comprises at least one of: (1) a predefined intensity level of light to be output by the indicator light source associated with the light pollution, wherein the predefined intensity level of the light comprises a percentage of a maximum luminosity of the indicator light source associated with the light pollution, (2) a predefined color of light to be output by the indicator light source associated with the light pollution, and (3) a predefined blink rate of light to be output by the indicator light source associated with the light pollution.

17. A system comprising one or more processors and memory storing one or more programs for execution by the one or more processors, the one or more programs including instructions that when executed by the one or more processors, cause the system to perform a method for reducing light pollution in a medical environment comprising:

determining that lighting in the medical environment is to be adjusted for use during a medical procedure, the lighting in the medical environment comprising light emitted by a medical light for illumination of a subject for observation during the medical procedure;

identifying a device in the medical environment that is communicatively connected to the system, the device including an indicator light source associated with the light pollution, the indicator light source configured to indicate a functionality of the device;

determining that a setting of the indicator light source associated with the light pollution is to be adjusted to a predefined setting associated with reducing the light pollution during the medical procedure; and causing the setting of the indicator light source associated with the light pollution to be adjusted to the predefined setting.

18. The system of claim 17, wherein determining that the lighting in the medical environment is to be adjusted comprises:

determining, using one or more optical sensors, that an ambient light of the medical environment has been adjusted for use during the medical procedure, the setting of the indicator light source associated with the light pollution being adjusted based at least in part on the ambient light.

19. A non-transitory computer-readable medium storing computer program instructions that, when executed by one or more processors of a system, cause the system to perform a method for reducing light pollution in a medical environment comprising:

determining that lighting of the medical environment is to be adjusted for use during a medical procedure, the lighting in the medical environment comprising light emitted by a medical light for illumination of a subject for observation during the medical procedure;

identifying a device in the medical environment that is communicatively connected to the system, the device including an indicator light source associated with the light pollution, the indicator light source configured to indicate a functionality of the device;

determining that a setting of the indicator light source associated with the light pollution is to be adjusted to a predefined setting associated with reducing the light pollution during the medical procedure; and causing the setting of the indicator light source associated with the light pollution to be adjusted to the predefined setting.

* * * * *